US011540783B2

(12) United States Patent
Bosque

(10) Patent No.: US 11,540,783 B2
(45) Date of Patent: Jan. 3, 2023

(54) ALARM SYSTEM FOR INTRAVENOUS PUMP OR CATHETER BASED UPON FUZZY LOGIC

(71) Applicant: University of Washington, Seattle, WA (US)

(72) Inventor: Elena M. Bosque, Pacifica, CA (US)

(73) Assignee: University of Washington, Seattle, WA (US)

(*) Notice: Subject to any disclaimer, the term of this patent is extended or adjusted under 35 U.S.C. 154(b) by 425 days.

(21) Appl. No.: 16/609,152

(22) PCT Filed: Apr. 27, 2018

(86) PCT No.: PCT/US2018/029901
§ 371 (c)(1),
(2) Date: Oct. 28, 2019

(87) PCT Pub. No.: WO2018/201018
PCT Pub. Date: Nov. 1, 2018

(65) Prior Publication Data
US 2020/0187870 A1 Jun. 18, 2020

Related U.S. Application Data

(60) Provisional application No. 62/491,865, filed on Apr. 28, 2017.

(51) Int. Cl.
A61B 5/00 (2006.01)
A61B 5/021 (2006.01)
(Continued)

(52) U.S. Cl.
CPC ............ A61B 5/746 (2013.01); A61B 5/0002 (2013.01); A61B 5/02141 (2013.01);
(Continued)

(58) Field of Classification Search
CPC .......... A61B 2503/04; A61B 2503/045; A61B 2503/06; A61B 2562/0247; A61B 5/0002;
(Continued)

(56) References Cited

U.S. PATENT DOCUMENTS 3,638,640 A 2/1972 Shaw
4,167,331 A 9/1979 Nielsen
(Continued)

OTHER PUBLICATIONS

International Search Report and Written Opinion dated Aug. 28, 2018, issued in corresponding International Application No. PCT/US2018/029901, filed Apr. 27, 2018, 11 pages.
(Continued)

Primary Examiner — Jonathan T Kuo
(74) Attorney, Agent, or Firm — Christensen O'Connor Johnson Kindness PLLC

(57) ABSTRACT

In some embodiments, a self-monitoring intravenous catheter system is provided. An alarm controller is provided that receives signals representing a pH value, an oxygen saturation value, and a pressure value in proximity to the distal end of the catheter. By performing a fuzzy logic analysis of the values, the alarm controller is able to detect that the catheter is about to fail or has failed, and can cause alerts to be presented. In some embodiments, an intravenous catheter is provided that has a pH sensor and an oximeter disposed at a distal end of the catheter to obtain the pH value and oxygen saturation values analyzed by the alarm controller. Embodiments of the catheter and self-monitoring intravenous catheter system may be particularly useful in treating neonates, who are sensitive to catheter failure and are not capable of detecting the signs of failure themselves.

23 Claims, 9 Drawing Sheets

(51) Int. Cl.
    *A61B 5/0215*     (2006.01)
    *A61B 5/145*     (2006.01)
    *A61B 5/1455*     (2006.01)
    *G06N 7/02*     (2006.01)
(52) U.S. Cl.
    CPC ........ *A61B 5/02152* (2013.01); *A61B 5/1455* (2013.01); *A61B 5/14539* (2013.01); *A61B 5/6852* (2013.01); *A61B 5/7264* (2013.01); *G06N 7/023* (2013.01); *A61B 2503/045* (2013.01); *A61B 2562/0247* (2013.01)
(58) Field of Classification Search
    CPC ... A61B 5/0205; A61B 5/021; A61B 5/02141; A61B 5/0215; A61B 5/02152; A61B 5/03; A61B 5/14539; A61B 5/1455; A61B 5/14551; A61B 5/4836; A61B 5/4839; A61B 5/6852; A61B 5/7264; A61B 5/746; A61M 2005/16868; A61M 2005/1726; A61M 2205/18; A61M 2205/3561; A61M 2205/505; A61M 2205/52; A61M 5/14212; G06N 7/023; G08B 21/00–21/0211
    See application file for complete search history.

(56) References Cited

U.S. PATENT DOCUMENTS

| | | | |
|---|---|---|---|
| 4,407,290 A | 10/1983 | Wilber | |
| 4,453,218 A | 6/1984 | Sperinde et al. | |
| 4,800,495 A | 1/1989 | Smith | |
| 5,339,818 A | 8/1994 | Baker et al. | |
| 5,355,880 A | 10/1994 | Thomas et al. | |
| 5,368,224 A | 11/1994 | Richardson et al. | |
| 5,494,032 A | 2/1996 | Robinson et al. | |
| 5,830,135 A * | 11/1998 | Bosque | G16H 50/20 600/323 |
| 6,898,585 B2 * | 5/2005 | Benson | G05B 9/02 700/50 |
| 7,246,620 B2 * | 7/2007 | Conroy, Jr. | A61B 5/14551 128/204.29 |
| 8,073,517 B1 * | 12/2011 | Burchman | A61B 5/6852 600/341 |
| 8,317,776 B2 * | 11/2012 | Ferren | A61B 5/412 604/891.1 |
| 8,403,881 B2 * | 3/2013 | Ferren | A61B 5/02055 604/65 |
| 8,870,813 B2 * | 10/2014 | Ferren | A61M 5/1723 604/66 |
| 9,504,781 B2 * | 11/2016 | Kassab | A61B 17/1214 |
| 2002/0105428 A1 * | 8/2002 | Benson | G05B 9/02 340/635 |
| 2004/0206353 A1 * | 10/2004 | Conroy, Jr. | A61B 5/417 128/204.23 |
| 2006/0111933 A1 * | 5/2006 | Wheeler | G06Q 10/06375 705/2 |
| 2008/0172013 A1 | 7/2008 | Kucklick | |
| 2009/0156988 A1 * | 6/2009 | Ferren | A61B 5/412 604/65 |
| 2009/0192367 A1 * | 7/2009 | Braig | A61B 5/150221 600/311 |
| 2010/0204765 A1 | 8/2010 | Hall et al. | |
| 2012/0078095 A1 * | 3/2012 | Heck | A61M 25/0102 604/510 |
| 2014/0148751 A1 * | 5/2014 | Kassab | A61M 1/3655 604/8 |

OTHER PUBLICATIONS

Agius, C.R., "Intelligent Infusion Technologies: Integration of a Smart System to Enhance Patient Care," Journal of Infusion Nursing 35(6):364-368, Nov./Dec. 2012.

Alpan, G., et al., "Heparinization of Alimentation Solutions Administered Through Peripheral Veins in Premature Infants: A Controlled Study," Pediatrics 74(3) 375-378, Sep. 1984.

Alkalay, A.L.,et al., "Central Venous Line Thrombosis in Premature Infants: A Case Management and Literature Review," American Journal of Perinatology 10(4):323-326, Jul. 1993.

Azimi, P.H., et al., "Malassezia Furfur: A Cause of Occlusion of Percutaneous Central Venous Catheters in Infants in the Intensive Care Nursery," The Pediatric Infectious Disease Journal 7(2):100-103, 1998.

Bansal, V., et al., "Central Line Perforation Associated with *Staphylococcus epidermidis* Infection," Journal of Pediatric Surgery 28(7):894-7, Jul. 1993.

Barnard, A., "A Critical Review of the Belief That Technology Is a Neutral Object and Nurses Are its Master," Journal of Advanced Nursing 26(1):126-131, 1997.

Bhananker, S.M., et al., "Liability Related to Peripheral Venous and Arterial Catheterization: A Closed Claim Analysis," Anesthesia & Analgesia 109(1):124-9, Jul. 2009.

Bosque, E., and Weaver, L., "Continuous Versus Intermittent Heparin Infusion of Umbilical Artery Catheters in the Newborn Infant," The Journal of Pediatrics 108(1):141-143, Jan. 1986.

Bosque, E.M., "Pulse Oximetry and Intuition in the Neonatal Intensive Care Unit," Critical Care Nursing Clinics of North America 7(2):219-225, Jun. 1995.

Bosque, E.M., "Symbiosis of Nurse and Machine Through Fuzzy Logic: Improved Specificity of a Neonatal Pulse Oximeter Alarm," Advances in Nursing Science 18(2):67-75, Dec. 1995.

Bosque, E.M., "Symbiosis of Nurse and Machine Through Fuzzy Logic: Improved Specificity of a New Neonatal Pulse Oximeter Alarm," doctoral dissertation, University of California, San Francisco, 1992, 162 pages.

Breaux, C.W., et al., "Calcium Phosphate Crystal Occlusion of Central Venous Catheters Used for Total Parenteral Nutrition in Infants and Children: Prevention and Treatment," Journal of Pediatric Surgery 22(9):829-832, Sep. 1987.

Brismar, B., et al., "Diagnosis of Thrombosis by Catheter Phlebography After Prolonged Central Venous Catheterization," Annals of Surgery 194(6):779-783, Dec. 1981.

Brown, A.S., et al., "Skin Necrosis From Extravasation of Intravenous Fluids in Children," Plastic & Reconstructive Surgery 64(2):145-150, Aug. 1979.

Buckley, J.J., and Siler, W., "A new T-norm," Fuzzy Sets and Systems 100:283-290, 1998.

Camara, D., "Minimizing Risks Associated With Peripherally Inserted Central Catheters in the NICU," MCN [The American Journal of Maternal/Child Nursing] 26(1):17-21, Jan./Feb. 2001.

Chen,T., et al., "Calcinosis Cutis Complicated by Compartment Syndrome Following Extravasation of Calcium Gluconate in a Neonate: A Case Report," Pediatrics and Neonatology 51(4):238-241, Aug. 2010.

Chen,C., et al., "Paraplegia: Complication of Percutaneous Central Venous Line Malposition," Pediatric Neurology 23(5):65-68, 2001.

Chowdhary, S.K., et al., "Central-venous Access Through the Peripheral Route in Surgical Neonates: An Audit of 125 Consecutive Lines From a Regional Neonatal Centre," Pediatric Surgery International 17(5-6):433-435, Jul. 2001.

Clark, T.M., et al., "New Multimodal Data Obtained In-vivo From a Single Ultra-miniature Transducer", Aug. 2015, Biomed Microdevices 17(4):72, Aug. 2015, 11 pages.

Clark, D., "Sony Enters Hand-Held Computer Field," The San Francisco Chronicle, Mar. 8, 1990, p. C3.

Clarke, P., et al., "Parenteral Nutrition Solution Retrieved by Lumbar Puncture Following Left Saphenous Vein Catheterization," Journal of Paediatrics and Child Health 39(5):386-389, Jul. 2003.

Damalerio, R., et al., "Biopackaging of Intracranial Pressure Microsystem for Multimodality Neuro Monitoring of Severe Head Injury Patients," 2016 IEEE 66th Electronic Components and Technology Conference (ECTC), Las Vegas, N.V., May 31-Jun. 3, 2016, p. 194-199.

Doellman, D., et al., "Infiltration and Extravasation," Journal of Infusion Nursing 32(4):203-211, Jul./Aug. 2009.

(56) References Cited

OTHER PUBLICATIONS

Duntley, P., et al., "Vascular Erosion by Central Venous Catheters. Clinical Features and Outcome," Chest 101(6):1633-1638, Jun. 1992.
Ekelund, H., et al., "Fibrinolysis in Newborns," Acta Paediatrica Scandinavica 59:33-43, 1970.
Evans, M., and Lentsch, D., "Percutaneously Inserted Polyurethane Central Catheters in the NICU: One Unit's Experience," Neonatal Network 18(6):37-46, Sep. 1999.
Fabian, B., "Intravenous Complication: Infiltration," Journal of Intravenous Nursing 23(4):229-231, Jul./Aug. 2000.
Foo, R., et al., "Complications in Tunneled CVL Versus PICC Lines in Very low Birth Weight Infants," Journal of Perinatology 21:525-530, 2001.
Friedman, J., "Plastic Surgical Problems in the Neonatal Intensive Care Unit," Clinics in Plastic Surgery 25(4):599-617, Oct. 1998.
Fullilove, S., and Fixsen, J., "Major Limb Deformities as Complications of Vascular Access in Neonates," Paediatric Anaesthesia 7:247-250, 1997.
Gault, D.T., "Extravasation Injuries," British Journal of Plastic Surgery, 46:91-96, 1993.
Gladman, G., et al., "*Staphylococcus epidermidis* and Retention of Neonatal Percutaneous Central Venous Catheters," Archives of Disease in Childhood 65(2):234-235, Feb. 1990.
Gnanalingham, M.G., et al., "Consensus on Neonatal Infusion Pumps and Pressure Monitoring," Archives of Disease in Childhood 90(1):F92-F94, 2005.
Gordon, K., and Dearmun, A.K., "Occlusion Problems in Central Venous Catheters: the Child and Family Perspective," Journal of Child Health Care 7(1):):55-69, 2003.
Goutail-Flaud, M.F., et al., Central Venous Catheter-Related Complications in Newborns and Infants: A 587-Case Survey, Journal of Pediatric Surgery 26(6):645-650, Jun. 1991.
Grisoni, E.R., et al., "Thrombosis and Infection Complicating Central Venous Catheterization in Neonates," Journal of Pediatric Surgery 21(9):772-776, Sep. 1986.
Haavind, R., "Fuzzy Logic", PC/Computing Magazine, Aug. 1989, pp. 147-149.
Hadaway, L.C., "Major Thrombotic and Nonthrombotic Complications," Journal of Intravenous Nursing 21(5S):S143-S160, Sep./Oct. 1998.
Harms, K., et al., "Randomized, Controlled Trial of Amoxicillin Prophylaxis for Prevention of Catheter-related Infections in Newborn Infants with Central Venous Silicone Elastomer Catheters," The Journal of Pediatrics 127(4):615-619, Oct. 1995.
Harris, T.S., and Von Maltzahn, W.W., "Infusion Line Model for the Detection of Infiltration, Extravasation, and Other Fluid Flow Faults," IEEE Transactions on Biomedical Engineering 40(2):154-162, Feb. 1993.
Haynes, S., "Infusion Phlebitis and Extravasation," The Professional Nurse, pp. 160-161, Dec. 1989.
Hecker, J.F., et al., "Failure of Intravenous Infusions in Neonates," Journal of Paediatrics and Child Health 27(3):175-179, 1991.
Hecker, J.F., et al., "Phlebitis and Extravasation ("Tissuing") with Intravenous Infusions," The Medical Journal of Australia 140(11):658-660, May 1984.
Hecker, J.F., "Potential for Extending Survival of Peripheral Intravenous Infusions," BMJ 304:619-624, Mar. 1992.
Herbst S.L., et al., "Vascular Access Devices: Managing Occlusion and Related Complications in Home Infusion," Infusion 4:1-32, 1998.
Hogan, M.J., "Neonatal Vascular Catheters and Their Complications," Radiologic Clinics of North America 37(6):1109-1125, Nov. 1999.
Hruszkewycz, V., et al., "Complications Associated With Central Venous Catheters Inserted in Critically Ill Neonates," Infection Control and Hospital Epidemiology 12(9):544-548, Sep. 1991.
Browner, W.S., et al., "Estimating Sample Size and Power," Designing Clinical Research Need More Info 139-150.
Browner, W.S., et al., "Estimating Sample Size and Power: Applications and Examples," Need More Info 65-94.
© 1998 Intravenous Nurses' Society, "Infiltration/Extravasation," Journal of Intravenous Nursing 21(1) Supplement 1: S36-S37, Jan./Feb. 1998.
© 1998 Intravenous Nurses' Society, "Oncology/Antineoplastic Therapy," Journal of Intravenous Nursing 21(1) Supplement 1:S28-S29, Jan./Feb. 1998.
Janes, M., et al., "A Randomized Trial Comparing Peripherally Inserted Central Venous Catheters and Peripheral Intravenous Catheters in Infants With Very Low Birth Weight," Journal of Pediatric Surgery 35(7):1040-1044, Jul. 2000.
Johnson, R.C., "Fuzzy Help for Expert System", Electronic Engineering Times, Jul. 23, 1990, pp. 37 and 42.
Johnson, R.C., "Japan Sets Fuzzy Group", Electronic Engineering Times, Sep. 3, 1990, pp. 18 and 24.
Kearns, P.J., et al, "Complications of Long-arm Catheters: A Randomized Trial of Central Versus Peripheral tip Location," Journal of Parenteral and Enteral Nutrution 20(1):20-24, Jan.-Feb. 1996.
Keeney, S.E., and Richardson, C.J., "Extravascular Extravasation of Fluid as a Complication of Central Venous Lines in the Neonate," Journal of Perinatology 15(4):284-288, 1995.
Kelly, R.E., et al., "Choosing Venous Access in the Extremely Low Birth Weight (ELBW) Infant: Percutaneous Central Venous Lines and Peripherally Inserted Catheters," Neonatal Intensive Care 10:15-18, Sep./Oct. 1997.
Krasna, I.H., and Krause, T., "Life-Threatening Fluid Extravasation of Central Venous Catheters," Journal of Pediatric Surgery 26(11):1346-1348, Nov. 1991.
Kumar, R.J., et al., "Management of Extravasation Injuries," ANZ Journal of Surgery 71:285-289, 2001.
"Nihon-zone," Leigh & Leigh, The Japan Times (Cartoons), Sep. 1, 1990, p. 13.
Lewis, G.B.H., and Hecker, J.F., "Changes in Local Venous Tone in Response to Infusions of Saline and Dextrose Solutions," Anaesthesia and Intensive Care 12(1):27-32, Feb. 1984.
Macklin, D., "Infusion Pump Therapy: A Guide for Clinicians and Educators," Hospira, Inc., Lake Forest, Illinois, Jun. 2008, 44 pages.
Macklin, D., "What's Physics got to do with it? A Review of the Physical Principles of Fluid Administration," Journal of Vascular Access Devices, pp. 7-11, Summer 1999.
Mactier, H., et al., "Central Venous Catheterisation in Very low Birthweight Infants," Archives of Disease in Childhood 61:449-453, 1986.
Maki, D.G. et al., "Infection Control in Intravenous Therapy," Annals of Internal Medicine 79(6):867-887, Dec. 1973.
Marsh, D., et al., "Right Atrial Thrombus Formation Screening Using Two-Dimensional Echocardiograms in Neonates With Central Venous Catheters," Pediatrics 81(2): 284-286, Feb. 1988.
McGee, D.C., and Gould, M.K., "Preventing Complications of Central Venous Catheterization," The New England Journal of Medicine 348(12):1123-1133, Mar. 2003.
Moclair, A.E., et al., "Prolonging the Survival of Peripheral Infusion Sites in Neonates With Low-Dose Heparin," The International Journal of Pharmacy Practice 1(4):198-201, Aug. 1992.
Mupanemunda, R.H., and MacKanjee, H.R., "A Life-Threatening Complication of Percutaneous Central Venous Catheters in Neonates," American Journal of Diseases of Children 146(2):1414-1415, Dec. 1992.
Nadroo, A.M., et al., "Changes in Upper Extremity Position Cause Migration of Peripherally Inserted Central Catheters in Neonates," Pediatrics 110(1):131-136, Jul. 2002.
Nadroo, A.M., et al., "Death as a Complication of Peripherally Inserted Central Catheters in Neonates," The Journal of Pediatrics 138(4):599-601, Apr. 2001.
Nour, S., et al., "Intra-Abdominal Extravasation Complicating Parenteral Nutrition in Infants,"Archives of Disease in Childhood, Fetal & Neonatal Edition 72(3):F207-F208, 1995.
Peters, M., et al., "Persistent Antithrombin III Deficiency: Risk Factor for Thromboembolic Complications in Neonates Small for Gestational age," The Journal of Pediatrics 105(2):310-314, Aug. 1984.

(56) References Cited

OTHER PUBLICATIONS

Pettit, J., "Assessment of Infants With Peripherally Inserted Central Catheters: Part 2. Detecting Less Frequently Occurring Complications," Advances in Neonatal Care 3(1):14-26, Feb. 2003.

Phelps, S.J., et al., "Inability of Inline Pressure Monitoring to Predict or Detect Infiltration of Peripheral Intravenous Catheters in Infants," Clinical Pharmacy 9(4):286-292, Apr. 1990.

Phelps, S.J., et al., "Infusion Technology for Predicting and Detecting Infiltration of Peripheral Intravenous Catheter Sites in Infants," Clinical Pharmacy 12(3):216-221, Mar. 1993.

Philip, J.H., "Model for the Physics and Physiology of Fluid Administration," Journal of Clinical Monitoring 5(2):123-134, Apr. 1989.

Bosque, E., "Neonatal Peripheral Intravenous (PIV) Catheter In-Line Pressure Natural History Study," Poster accepted for presentation at the 40th District XIII Conference on Perinatal Pediatrics, Honolulu, HI, Jul. 2016.

Bosque, E., "Neonatal Peripheral Intravenous (PIV) Catheter In-Line Pressure Natural History Study," Abstract accepted for presentation at the 40th District XIII Conference on Perinatal Pediatrics, Honolulu, HI, Jul. 2016.

Bosque, E., "Neonatal Peripheral Intravenous (PIV) Catheter In-line Pressure Natural History Study," 16 pages.

Porcelli, P.J., et al., "A Linear Regression Model to Predict the pH of Neonatal Parenteral Nutrition Solution," Journal of Clinical Pharmacy and Therapeutics 25:55-59, 2000.

Puntis, J.W.L., et al., "Staff Training: A Key Factor in Reducing Intravascular Catheter Sepsis," Archives of Disease in Childhood 65:335-337, 1990.

Schwartz, T.J., "Fuzzy Systems in the Real World," AI Expert 5(8):29-36, Aug. 1990.

Scott, D.A., et al., "Detection of Intravenous Fluid Extravasation Using Resistance Measurements," Journal of Clinical Monitoring 12(4):325-330, Jul. 1996.

Sierchio, G.P., "A Multidisciplinary Approach for Improving Outcomes," Journal of Infusion Nursing 26(1):34-43, Jan./Feb. 2003.

Siler, W., and Martens, J., "Hemodynamic Alarm System for Pulmonary Artery Catheters in an Intensive Care Unit," Proceedings of the Joint 9th IFSA World Congress and 20th NAFIPS International Conference, Vancouver, BC, Canada, Jul. 25-28, 2001, pp. 1967-1972.

Sonohata, M., et al., "Neonate With Calcinosis Cutis Following Extravasation of Calcium Gluconate," Journal of Orthopaedic Science 13:269-272, 2008.

Stranz, M., "Adjusting pH and Osmolarity Levels to fit Standards and Practices,"Journal of Vascular Access Devices 7:12-17, Fall 2002.

Stovroff, M., and Teague, W.G., "Intravenous Access in Infants and Children," Pediatric Clinics of North America 45(6):1373-1393, Dec. 1998.

Subhani M., et al., "Phentolamine Use in a Neonate for the Prevention of Dermal Necrosis Caused by Dopamine: A Case Report," Journal of Perinatology 21:324-326, 2001.

Tanase, D., et al., "Investigation of Multi-Sensor Techniques for Cardiac-Output Measurements in Intensive Care," Proceedings of the Third IEEE/EMBS Special Topic Conference on Microtechnologies in Medicine and Biology, Kahunku, Oahu, Hawaii, May 12-15, 2005, pp. 122-125.

Tanase, D., et al., "Multi-Parameter Sensor System with Intravascular Navigation for Catheter/Guide Wire Application," Sensors and Actuators A Physical, 97-98:116-124, 2002.

Tobin, C.R., "The Teflon Intravenous Catheter: Incidence of Phlebitis and Duration of Catheter Life in the Neonatal Patient," Journal of Obstetric, Gynecologic, and Neonatal Nursing 1:35-42, Jan./Feb. 1988.

Treas, L.S., and Latinis-Bridges, B., "Efficacy of Heparin in Peripheral Venous Infusion in Neonates," Journal of Obstetric, Gynecologic, and Neonatal Nursing 21(3):214-219, May/Jun. 1992.

Trotter, C.W., "Percutaneous Central Venous Catheter-Related Sepsis in the Neonate: An Analysis of the Literature from 1990 to 1994," Neonatal Network 15(3):15-28, Apr. 1996.

Uvizl, R., et al., "Biochemical Changes in the Patient's Plasma After red Blood Cell Transfusion," Signa Vitae 6(2):64-71, 2011.

Wallich, P., "Software 'Doctor' Prescribes Remedies," IEEE Spectrum, Oct. 1986, pp. 43-48.

Williams, E.C., "Catheter-Related Thrombosis," Clinical Cardiology 13:VI-34-V1-36, Apr. 1990.

Wright, A., "Reducing Infusion Failure: A Pharmacologic Approach—A Review," Journal of Intravenous Nursing 19(2):89-97, Mar./Apr. 1996.

Wynsma, L.A., "Negative Outcomes of Intravascular Therapy in Infants and Children," AACN Clinical Issues 9(1):49-63, Feb. 1998.

Ying, H., "An Expert System-Shell-Based Fuzzy Controller: Theory, Development, and Application to the Control of Postsurgical Hypertension," doctoral dissertation, University of Alabama at Birmingham, Birmingham, Alabama, 1990, 76 pages.

Yosowitz, P., et al., "Peripheral Intravenous Infiltration Necrosis," Annals of Surgery 182(5):553-556, Nov. 1975.

Zadeh, L.A., "Fuzzy Sets," Information and Control 8(3):338-353, 1965.

Zimrin, A.B., and Hess, J.R., "Current Issues Relating to the Transfusion of Stored Red Blood Cells," Vox Sanguinis 96:93-103, 2009.

\* cited by examiner

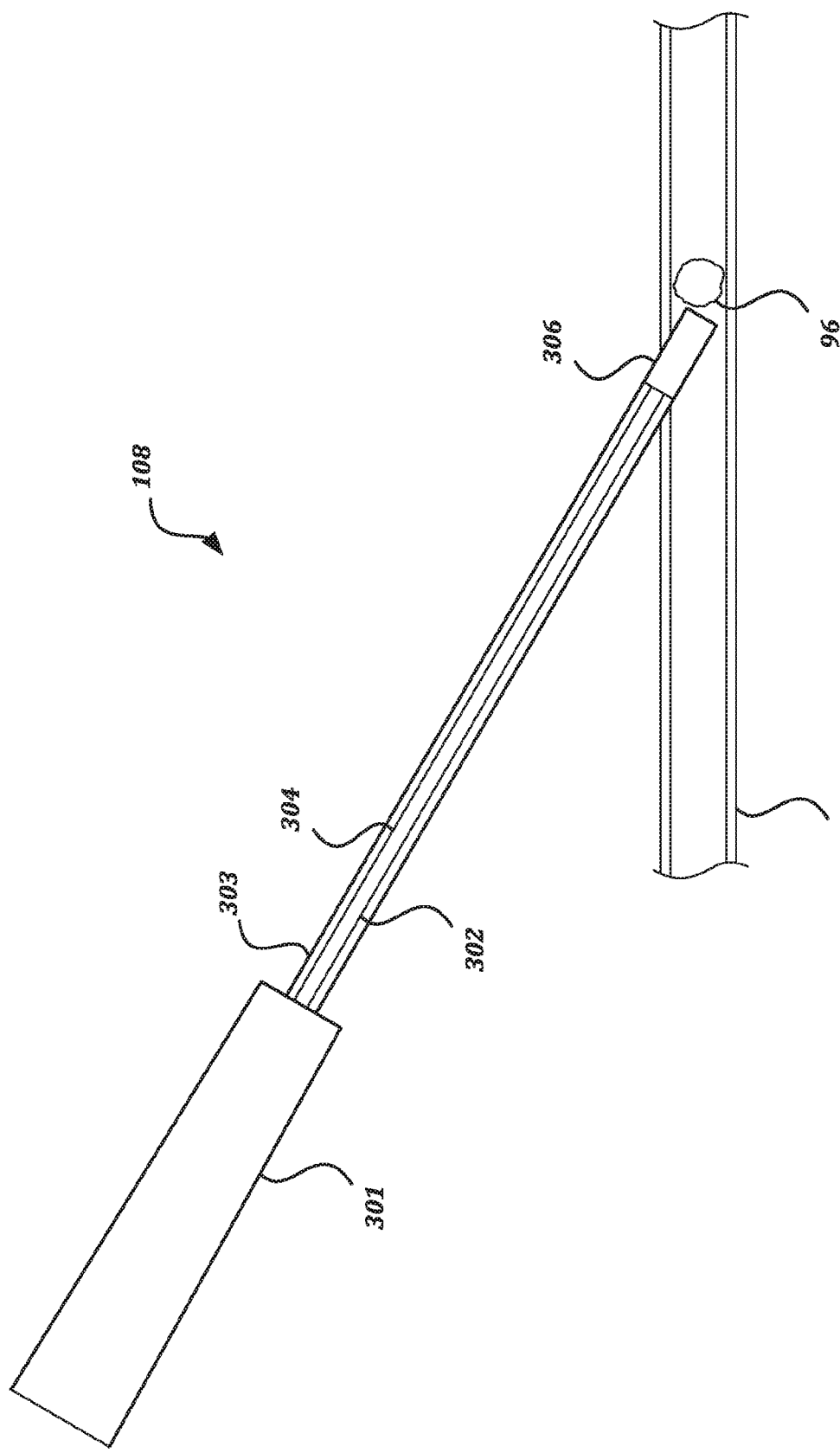

ALARM SYSTEM FOR INTRAVENOUS PUMP OR CATHETER BASED UPON FUZZY LOGIC

CROSS-REFERENCE(S) TO RELATED APPLICATION(S)

This application is a National Stage of International No. PCT/US2018/029901, filed on Apr. 27, 2018, which claims the benefit of Provisional Application No. 62/491,865, filed Apr. 28, 2017, the entire disclosure of which is hereby incorporated by reference herein for all purposes.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In some embodiments, a self-monitoring intravenous catheter system is provided. The self-monitoring intravenous catheter system comprises a catheter having a proximal portion and a distal end; a pump device coupled to the proximal portion of the catheter; and a set of sensors, including at least an oximeter and a pH sensor located at the distal end of the catheter.

In some embodiments, an alarm controller for a self-monitoring intravenous catheter system is provided. The alarm controller comprises at least one processor; a sensor interface configured to receive signals from at least an oximeter and a pH sensor; and a nontransitory computer-readable medium. The computer-readable medium has computer-executable instructions stored thereon which, in response to execution by the at least one processor, cause the alarm controller to monitor the signals from at least the oximeter and the pH sensor; and in response to determining that the signals indicate a failure of a catheter, cause an alert to be presented.

In some embodiments, a catheter is provided. The catheter comprises a tube having a proximal portion and a distal end; an oximeter located at the distal end of the tube; and a pH sensor located at the distal end of the tube.

In some embodiments, a method of automatically monitoring a status of an intravenous catheter is provided. A processor of an alarm controller receives a set of signals from at least one of a pH sensor and an oximeter. The processor performs a fuzzy logic analysis based on the signals to determine a catheter status value. In response to determining that the catheter status value indicates failure of the catheter, the processor causes an alert to be presented. In some embodiments, a nontransitory computer-readable medium having instructions stored thereon which, in response to execution by one or more processors of an alarm controller, cause the alarm controller to perform such a method. In some embodiments, an alarm controller is provided that comprises at least one processor, a sensor interface configured to receive signals from at least an oximeter and a pH sensor, and a nontransitory computer-readable medium having computer-executable instructions stored thereon which, in response to execution by the at least one processor, cause the alarm controller to perform such a method.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 is a schematic diagram that illustrates component details of an example embodiment of a catheter for use with a self-monitoring intravenous catheter system according to various aspects of the present disclosure;

DETAILED DESCRIPTION

Figure 1:
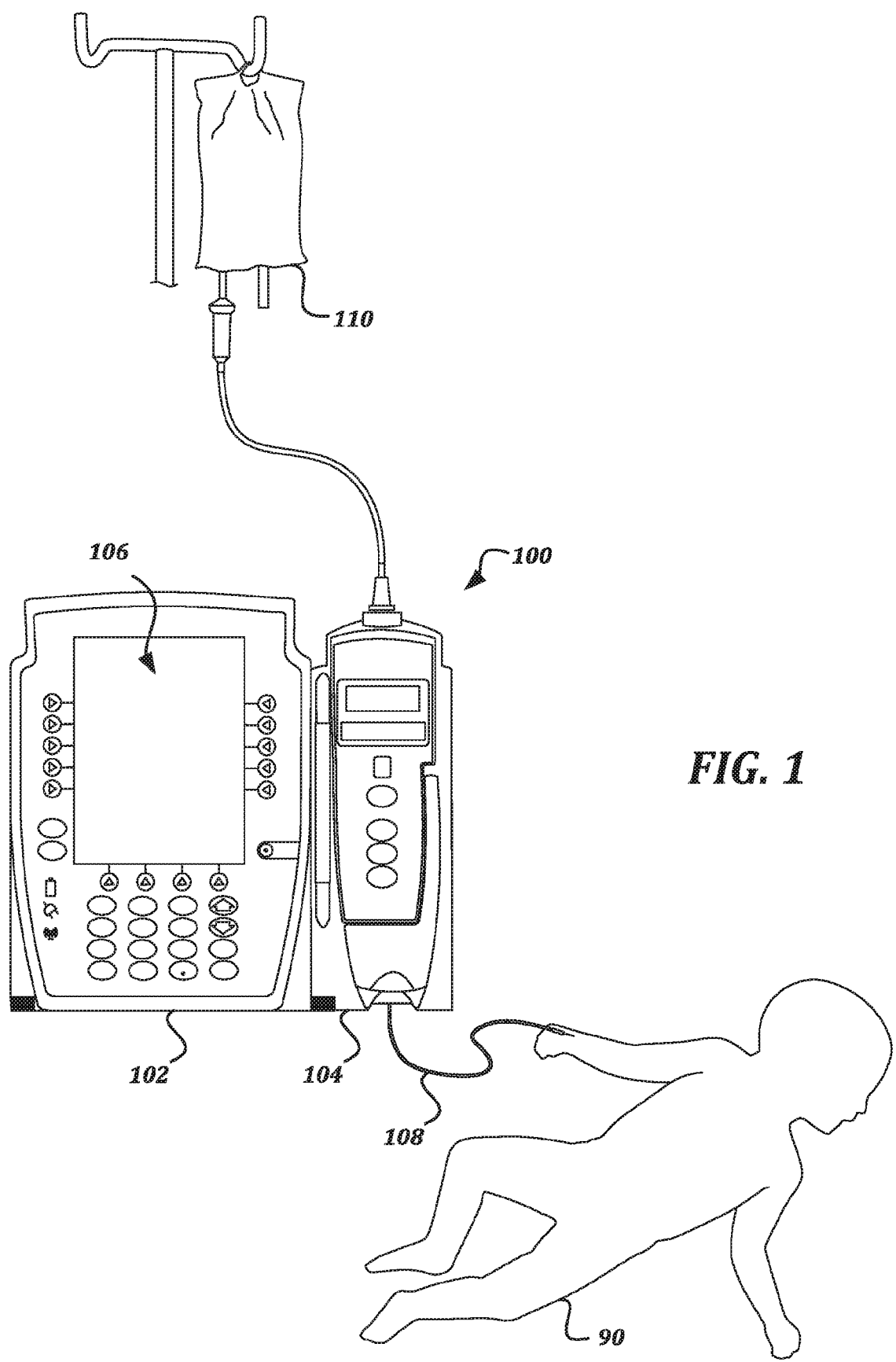
FIG. 1 is a schematic diagram that illustrates the use of an example embodiment of a self-monitoring intravenous catheter and pump system according to various aspects of the present disclosure.

Peripheral venous catheters in sick infants are necessary for the delivery of fluids, nutrition, and medications. Peripheral intravenous ("PIV") catheters have been associated with extravasation, edema, sequestration of medications and caustic solutions, and skin necrosis. Peripherally inserted central venous catheters ("PICC") have been associated with leaking, obstruction, infection, cardiac tamponade, neurological problems, and even death. Iatrogenic sequelae from PIV's and PICC's have been identified as one of the leading causes of adverse incidents and injury in hospitals, with rates as high as 78% and 62%, respectively.

Methods to increase the survival of intravenous infusion sites in neonatal populations have included avoidance of hyperosmolar solutions, neutralization of total parenteral nutrition, addition of heparin, implementation of inline filtration, amoxicillin prophylaxis, and aseptic techniques for insertion and catheter maintenance. Rescue interventions for occluded catheters have included flushing with saline, heparin, urokinase, and alteplase. Conscientious monitoring for signs of complications has been recommended as a way to reduce morbidity and mortality related to PIV's and PICC's in the NICU. Similar interventions may improve survival in other populations, as well. Presently, monitoring systems are dependent upon in-line measures of intraluminal pressure and resistance to trigger alarms when outside preset limits. However, in a few, limited studies, pressure or resistance measures or alarms have not been shown to be predictive of IV infiltration but may ring only after the extravasation, when the pressure in the tissue compartment has increased. Pressure is just one of various factors that affect the physics of flow of the neonatal PIV catheter and infusion pump system. These factors include fluid flow rate, pressure, resistance, viscosity, and the length of each component of the IV administration system. In older populations, pressure has been studied as a possible predictor of impending catheter infusion failure, but in the neonatal population, these principles have limited applicability since the overall flow rates, in most cases, are relatively low.

Infants cannot speak for themselves and cannot call for help when experiencing the initial signs of discomfort, pain, edema, or erythema, making this problem particularly acute in the neonatal population. Therefore, it would be desirable for an intravenous pump system to be outfitted with an alarm which can alert a health care provider to impending catheter failure in infants and other patients. The problem is to use variables whose characteristics are different when IV catheters are about to fail versus when they are situated properly.

There have been few published studies of monitoring as a way to detect problems with intravenous catheters. Phelps et al. studied intraluminal pressure in 44 infants and resistance in 52 infants under one year of age (median, 1 month) and found that intraluminal pressure changes predicted only 25% and resistance changes predicted 4% of PIV infiltrations. Fluid flow in the human intravenous system has been represented by a model which depicts physical devices as ideal resistors, pressure sources, and flow sources, and the venous system as a combination of ordinary and Starling resistors (Philip, 1989). Normal intravenous flows can be represented by the pressure-flow relationship where pressure=flow x resistance. However, it has been suggested that the current infusion devices may not behave as predicted during adverse situations because of physiological changes, which affect the pressure-flow relationship. During extravasation, tissue pressure is lower than venous pressure until the fluid fills the tissue compartment. This may explain why pressure or resistance measures or alarms have not been shown to be predictive of intravenous infiltration but may ring only after the extravasation, when the pressure in the tissue compartment has increased.

Although there are no published studies of measures of pH at the tip of the peripheral intravenous catheter, the normal pH of neonatal parenteral nutrition has been measured and determined to vary little, from one preparation facility. Porcelli et al. (2000) measured the pH of 135 samples of neonatal parenteral nutrition solution and developed a linear regression model, with which they predicted the pH of another 70 neonatal parenteral solutions. The measured pH was 5.364+0.110 (mean±SD, range 5.03-5.73). The absolute mean pH difference between the predicted and measured value for the 70 test samples was 0.04+0.04 ($r2=0.77$).

Based upon published theoretical causes, a neonatal PIV catheter may fail if occluded by various types of matter, either directly, as in the case of a fibrin clot, or indirectly, e.g. as a result of inflammation related to phlebitis after movement of the catheter (Ekelund, 1970; Maki, 1973; Peters, 1984; Pettit, 2003; Tobin, 1984; Wright, 1996). The pH of catheters about to fail, because of occlusion from fibrin, microbial matter, other foreign matter, or obstruction against tissue, may be different from those that are patent. To investigate this phenomenon, a study was conducted to measure the pH of PIV catheter tips removed from neonates because of failure versus elective removal. The study included a convenience sample of discarded PIV catheter tips (25G) after use from 47 neonates in a tertiary Level NICU.

Catheter infusion failure was defined as failure of a catheter infusion site to function while needed. Upon removal of a PIV catheter, one inch of the catheter tip was cut off and placed in a sterile test tube and labeled with catheter insertion date, removal date and reason for removal (Failure or Elective Removal) noted by the nurse who cared for the infant. The labeled catheter tips were tested in batches. One milliliter of sterile water was placed in a test tube and the pH of the solution was measured using a calibrated pH Meter (Oaklon Instruments, Vernon Hills, Ill.). The meter was calibrated, on each day of testing, with known calibrating solutions with pH of 4, 7, and 10.

Differences in pH between PIV catheters removed because of catheter infusion failure, versus electively, was compared using independent t-tests with significance alpha (two-sided)=0.05 and beta=0.20 (Hulley et al., 2007). There were 47 catheter tips collected in the convenience sample. Thirty-two were removed because of catheter infusion failure. Fifteen of the PIV catheters were removed, electively, because they were not needed. The pH (mean±S.D.) of PIV catheters removed because of failure was significantly lower than those removed electively (5.94±0.21, N=32 vs. 6.08±0.19, N=15; P=0.039). There was no significant difference in the time from removal to analysis between the catheters removed because of failure versus those removed electively.

The pH may have been lower in the catheter infusion failure group if there was material in the lumen at the tip, comprised of fibrin or other red blood cell products. It is known that serum acidification will occur in stored blood, over time, due to increased lactate, a metabolite of anaerobic metabolism of red blood cells. (Uvizl et al, 2011). The catheters removed electively, presumably, may have had fewer red blood cells, or other, material at the tips, since they were functioning without known problems at the time of removal. The catheter tips were analyzed in batches, but there was no significant difference in the time from removal to analysis between the groups.

The pH may have been lower in the catheter infusion failure group if there were some other material at the failed catheter tips with a pH that was lower than parenteral nutrition, which was infused via most of the PIVs, as common practice in the NICU where the samples were obtained. In Porcelli et al.'s (2000) predictive regression modeling study, the neonatal parenteral solution pH of the total 205 samples was 5.36+0.11 (mean±SD, range 5.03-5.73). The pH of some of the catheter tips removed electively in this study were within range of predicted values for neonatal parenteral nutrition, which, we assume, was the solution which had infused through most of the catheters in the study. This is what we would expect if a catheter were removed electively, when it was still functioning.

If some process occurred that affected the lumen or tip of a catheter, resulting in catheter infusion failure, then the pH may be one of a number of characteristics that may change, whether or not this is due to fibrin, red blood cells, or other materials at the tip. It may not be necessary, ultimately, to identify the process that produced the change in pH. The finding that the pH of the catheter groups was different indicates that one may be able to differentiate between catheter tips that are occluded or obstructed from those that are operating properly in vivo.

In embodiments of the present disclosure, a self-monitoring intravenous catheter system is provided. The catheter may have sensors arranged at its distal end that are configured to measure various characteristics of the environment at the distal end of the catheter, such as a pH value or an oxygen saturation value. Fuzzy logic may then be used on these characteristics to indicate normal and abnormal conditions, and thereby provide alerts when a catheter is likely to fail. Such techniques can help avoid injury to patients caused by failed catheters, particularly in neonates and other patients that cannot communicate or understand the signs of catheter failure. Such techniques can also improve the administration of care, in that the automated detection of impending failure, instead of requiring a physical examination to detect failure, allows electronic alerts to be transmitted from a pump system to a remote monitoring location. By conducting the fuzzy logic analysis of pH, oxygen saturation, and pressure, the self-monitoring intravenous catheter system is given new functionality that was not currently present in intravenous catheter systems, at least in that previous systems could not accurately predict or detect catheter failure, particularly in neonates.

FIG. 1 is a schematic diagram that illustrates the use of an example embodiment of a self-monitoring intravenous catheter and pump system according to various aspects of the present disclosure. In some respects, the self-monitoring intravenous catheter and pump system 100 is similar to other infusion pump systems. For example, the system 100 includes a pump system 102 and a pump 104. The pump 104 performs the physical act of pumping fluid through a catheter, while the pump system 102 provides control signals for controlling operation of the pump 104. The catheter 108 is operably coupled to the pump 104, such as having the catheter 108 physically threaded through a mechanism of the pump 104. A proximal end of the catheter 108 is coupled to a fluid bag. A distal end of the catheter 108 is inserted into a blood vessel of a patient 90. In use, the pump 104 applies pressure to fluid that enters the catheter from the fluid bag 110, such as medication or parenteral nutrition solution, to cause the fluid to travel through the catheter 108 and into the patient 90. The pump system 102 may have a variety of user interface devices thereon for controlling operation of the pump system 102 such as buttons or dials. The pump system 102 may also include a display 106 for presenting visual indicators of pump status, configuration values, alerts, warnings, and/or the like. Further details regarding the system 100 are described below.

Figure 2:
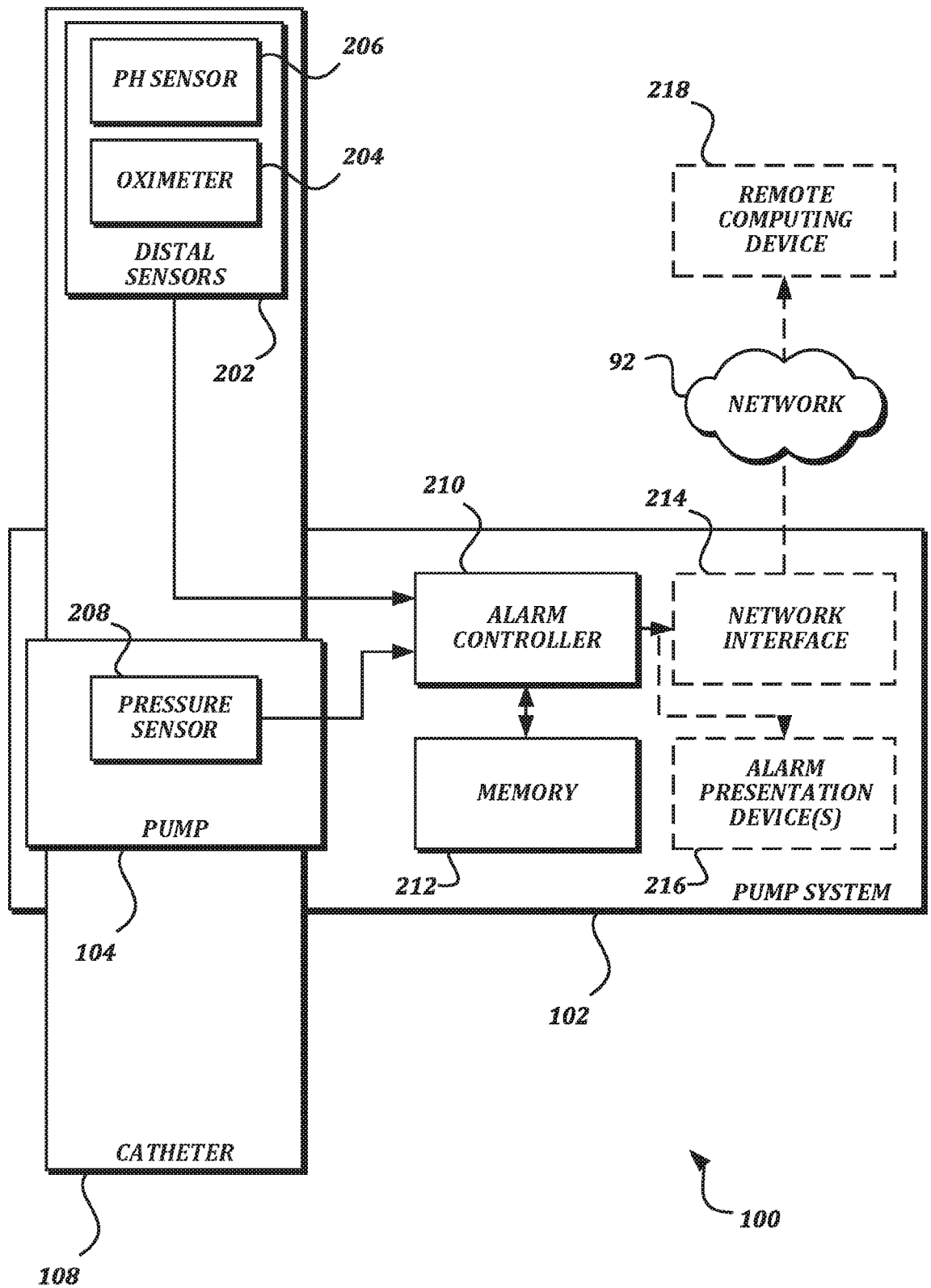
FIG. 2 is a block diagram that illustrates component details of an example embodiment of a self-monitoring intravenous catheter system according to various aspects of the present disclosure.

FIG. 2 is a block diagram that illustrates component details of an example embodiment of a self-monitoring intravenous catheter system according to various aspects of the present disclosure. As shown, the system 100 includes a pump system 102 and a catheter 108. A pump controller (not illustrated) of the pump system 102 controls operation of a pump 104. The pump 104 includes a mechanism (not illustrated) that physically interacts with the catheter 108 to pump fluid through the catheter 108. In some embodiments, the pump 104 includes a pressure sensor 208 configured to determine an amount of back pressure that is generated in the distal portion of the catheter 108. This allows the pump system 102 to monitor and control the amount of fluid that is delivered. In some embodiments, the pressure sensor 208 may be located outside of the pump 104, instead of inside of the pump 104 as illustrated.

As shown, the pump system 102 includes an alarm controller 210, a memory 212, a network interface 214, and one or more alarm presentation devices 216. In some embodiments, both the network interface 214 and the alarm presentation devices 216 may be present. In some embodiments, only one of the network interface 214 or the alarm presentation devices 216 may be present.

In some embodiments, the alarm controller 210 includes one or more computer processors configured to receive signals from one or more sensors and to process the signals to determine a state of the catheter 108. In some embodiments, the processors of the alarm controller 210 may also be configured to cause visual or audible notifications to be presented based on the determined state of the catheter 108. In some embodiments, the alarm controller 210 may include an ASIC, an FPGA, or other hardware device that has been configured to perform the tasks described herein. In some embodiments, the alarm controller 210 may be a general purpose processor that is configured to read instructions from a computer-readable medium to cause the alarm controller 210 to perform the tasks described herein. The computer-readable medium may be any type of computer-readable medium including but not limited to a ROM, an EEPROM, a flash memory, or a magnetic drive.

In some embodiments, the memory 212 is configured to store sensor values and other values determined by the alarm controller 210, and to provide the stored values to the alarm controller 210 when requested. In some embodiments, the memory 212 may include any suitable form of computer-readable medium, including but not limited to a flash memory, a magnetic drive, or RAM.

In some embodiments, the alarm presentation devices 216 are configured to receive commands from the alarm controller 210 to present visual or audible notifications. In some embodiments, one or more alarm presentation devices 216 may be present. Some non-limiting examples of alarm presentation devices 216 include an LCD display, a touchscreen display, an indicator light, an LED display, and a loudspeaker.

In some embodiments, the network interface 214 is configured to receive commands from the alarm controller 210 for visual or audible notifications to be presented, and to transmit the commands to a remote computing device 218 via a network 92. The remote computing device 218 may then present the notifications on a display or via a loudspeaker. The remote computing device 218 may also store the notifications for future reference. The network 92 may include any suitable types of wired or wireless network communication technologies, including but not limited to Ethernet, USB, Firewire, Bluetooth, WiFi, WiMAX, 3G, 4G, LTE, and the Internet, and the network interface 214 may be configured to communicate via one or more of these technologies. In some embodiments, the remote computing device 218 may be a desktop computing device, a laptop computing device, a tablet computing device, a smartphone, a server computing device, or a cloud computing service. In some embodiments, the pump system 102 may be located in a room with a patient, and the remote computing device 218 may be located at a remote monitoring station, such as a nurses' station or a telehealth service center.

The catheter 108 includes a set of distal sensors 202 located at the distal end of the catheter 108. As illustrated, the set of distal sensors 202 includes a pH sensor 206 to detect a pH value at the distal end of the catheter 108 and an oximeter 204 to detect an oxygen saturation value at the distal end of the catheter 108. The oximeter 204 may be any suitable type of oximeter for use with a catheter, such as a CO-oximeter, and may measure any type of oxygen saturation ($SO_2$), such as arterial oxygen saturation ($SaO_2$) or venous oxygen saturation ($SvO_2$). In some embodiments, only one of the pH sensor 206 or the oximeter 204 may be present in the set of distal sensors 202. In some embodiments, more sensors may be included in the set of distal sensors 202. Further illustration and discussion of an example embodiment of the structure of the catheter 108 and the set of distal sensors 202 is provided below.

The set of sensors of the system 100, including the set of distal sensors 202 and the pressure sensor 208, all provide signals indicating values associated with the various sensors to the alarm controller 210. The alarm controller 210 may store the values in the memory 212. The alarm controller 210 may also convert the values into fuzzy linguistic values, which may also be stored in the memory 212. The alarm controller 210 also processes the values in order to determine a state of the catheter 108, and causes warnings and alerts to be presented by the alarm presentation devices 216 and/or the remote computing device 218 based on the determined state of the catheter 108. A detailed description of processing performed by an example embodiment of the alarm controller 210 is provided below.

FIG. 3 is a schematic diagram that illustrates component details of an example embodiment of a catheter for use with a self-monitoring intravenous catheter system according to various aspects of the present disclosure. Details of the distal portion of the catheter 108 are shown in the FIGURE. Similar to many catheters, the catheter 108 includes a hub 301 and a tube 303. Unlike other catheters, however, the catheter 108 includes one or more sensors 306 at the distal end of the tube 303. In some embodiments, the sensors 306 are communicatively coupled to one or more conductors 302, 304 that travel back the length of the tube 303 and can be communicatively coupled to the alarm controller. In some embodiments, the conductors 302, 304 are embedded within the material of the tube 303 such that the interior area of the tube 303 is not reduced (thereby avoiding a restriction of fluid flow) and the exterior area of the tube 303 is not increased (thereby avoiding an increase in likelihood of damage to the blood vessel and/or surrounding tissue). In some embodiments, the conductors 302, 304 may be omitted if the sensors 306 can communicate wirelessly with the alarm controller 210, either using a power source embedded within the sensors 306, or by reflecting a signal from or drawing power from a wireless interrogation signal transmitted to the sensors 306.

In some embodiments, more than one separate sensor device 306 may be located at the distal end of the tube 303, such as separate oximeter and pH sensor devices. In some embodiments, an oximeter and a pH sensor may be combined into a single multi-modal sensor device positioned at the distal end of the tube 303. As shown, in some embodiments the sensors 306 are located such that they wrap around a portion of a distal outer surface of the tube 303, extending proximally for a suitable distance from the distal tip in order to obtain sensor values from the region immediately adjacent to the distal tip of the tube 303. In some embodiments, the sensors 306 may also cover a flat surface of the distal tip of the tube 303.

As shown, the distal tip of the catheter 108 is inserted into a blood vessel 94. As discussed above, the presence of an obstruction 96 can cause the pH value, the oxygen saturation value, and/or the pressure value obtained by the sensors to change in ways that can be detected by the pump system 102. Other failures, such as the distal tip of the catheter 108 passing through the blood vessel 94 into the surrounding tissue, can also be detected.

Figure 4A:
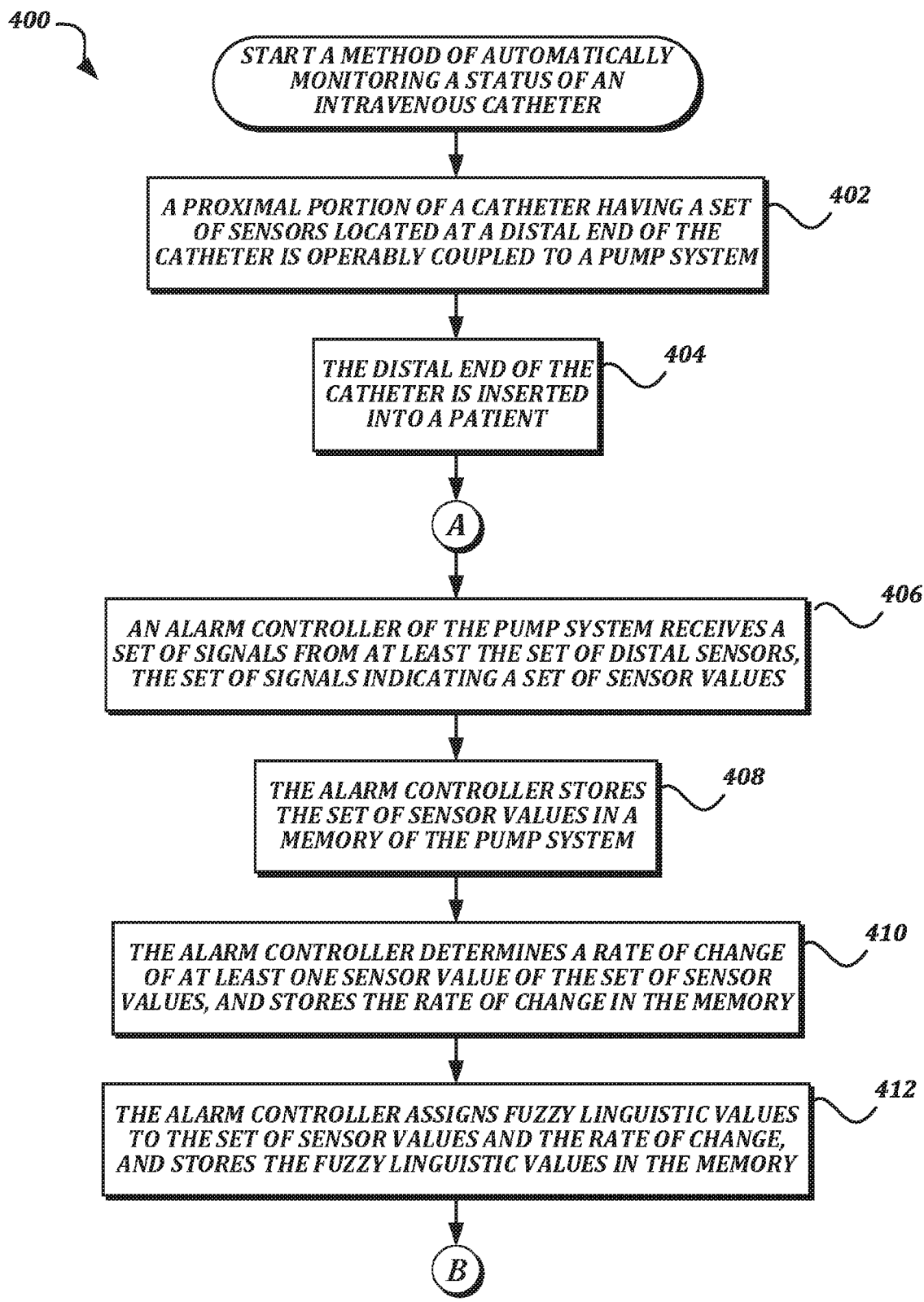
FIGS. 4A-4B are a flowchart that illustrates an example embodiment of a method of automatically monitoring a status of an intravenous catheter according to various aspects of the present disclosure.
Figure 4B:
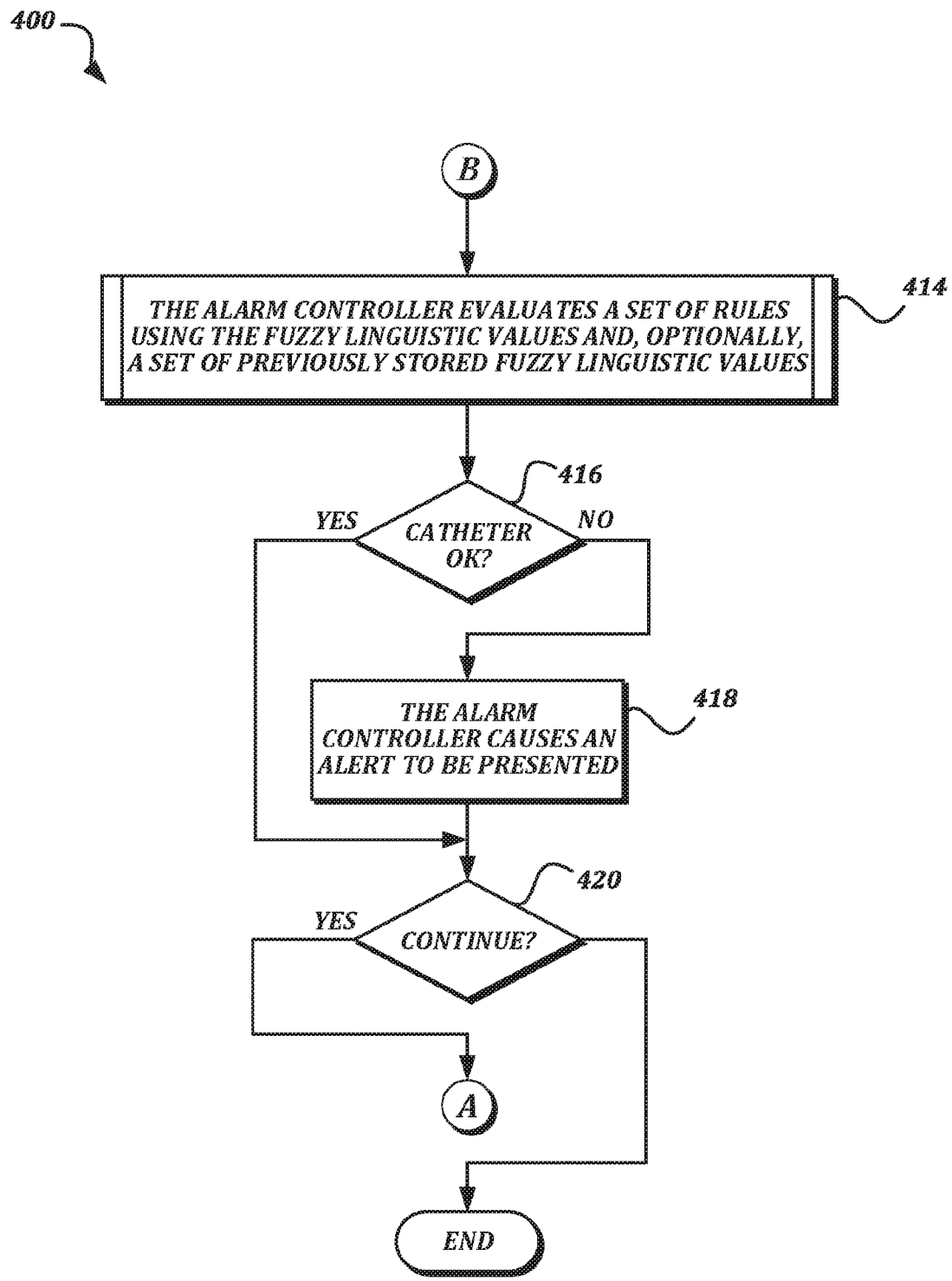

FIGS. 4A-4B are a flowchart that illustrates an example embodiment of a method of automatically monitoring a status of an intravenous catheter according to various aspects of the present disclosure. From a start block, the method 400 proceeds to block 402, where a proximal portion of a catheter 108 having a set of sensors 202 located at a distal end of the catheter 108 is operably coupled to a pump system 102. In some embodiments, the proximal portion of the catheter 108 may be fed through or placed within physical pump 104 as illustrated in FIG. 1. Though not illustrated in the flowchart, it is assumed that a furthest proximal end of the catheter 108 is connected to a fluid source to be administered. In some embodiments, operably coupling the catheter 108 to the pump system 102 includes communicatively coupling the set of sensors 202 to the alarm controller 210. The communicative coupling may use any suitable technique, including but not limited to physically coupling the conductors 302, 304 of the tube 303 to an interface within the pump system 102, wirelessly pairing the set of sensors 202 with the pump system 102, or locating the conductors 302, 304 within the pump system such that the pump system 102 can inductively detect the signals generated in the conductors 302, 304 without a direct electrical connection.

At block 404, the distal end of the catheter 108 is inserted into a patient. Techniques known to those of ordinary skill in the art for inserting catheters 108 into patients may be used. Further, traditional techniques known to those of ordinary skill in the art may be used to verify that the initial insertion of the catheter 108 was successful. If inserted correctly, the distal sensors 202 will be located within a target blood vessel.

The method 400 then proceeds through a continuation terminal ("terminal A") to block 406, where an alarm controller 210 of the pump system 102 receives a set of signals from at least the set of distal sensors 202, the set of signals indicating a set of sensor values. In some embodiments, the signals may indicate analog values which are converted to digital values by the alarm controller 210. In some embodiments, analog signals may pass through an A/D converter (not illustrated) before being received by the alarm controller 210. In some embodiments, the set of signals may also include signals from sensors that are not located at the distal end of the catheter 108, such as the pressure sensor 208.

At block 408, the alarm controller 210 stores the set of sensor values in a memory 212 of the pump system 102. In some embodiments, the alarm controller 210 may store the set of sensor values as an entry in a time series stored in the memory 212. In some embodiments, the entry may include a timestamp. In some embodiments, the entry may be appended to the time series without a timestamp, and a standard amount of time between sensor readings may be used to interpret the time series. At block 410, the alarm controller 210 determines a rate of change of at least one sensor value of the set of sensor values, and stores the rate of change in the memory 212. In some embodiments, the alarm controller 210 may use one or more previously stored sets of sensor values to determine the rate of change.

At block 412, the alarm controller 210 assigns fuzzy linguistic values to the set of sensor values and the rate of change, and stores the fuzzy linguistic values in the memory. In some embodiments, the rate of change calculations may be optional, in which case fuzzy linguistic values may not be assigned or stored for the rate of change.

Figure 5A:
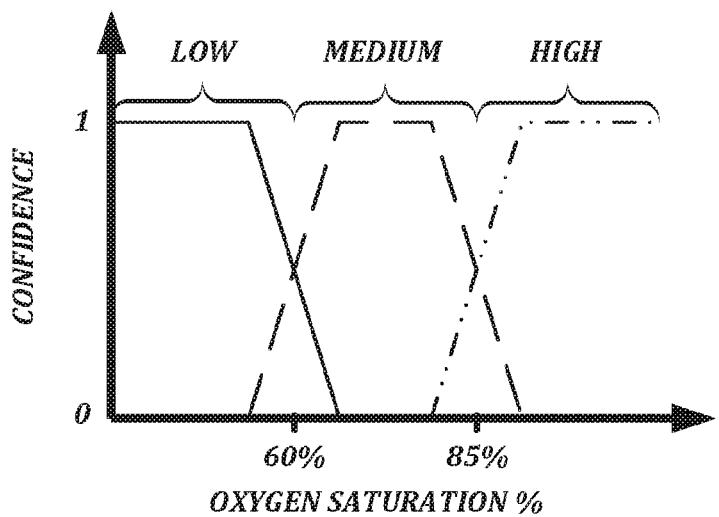
FIGS. 5A-5C are charts that illustrate examples of the assignment of fuzzy linguistic values according to various aspects of the present disclosure.
Figure 5B:
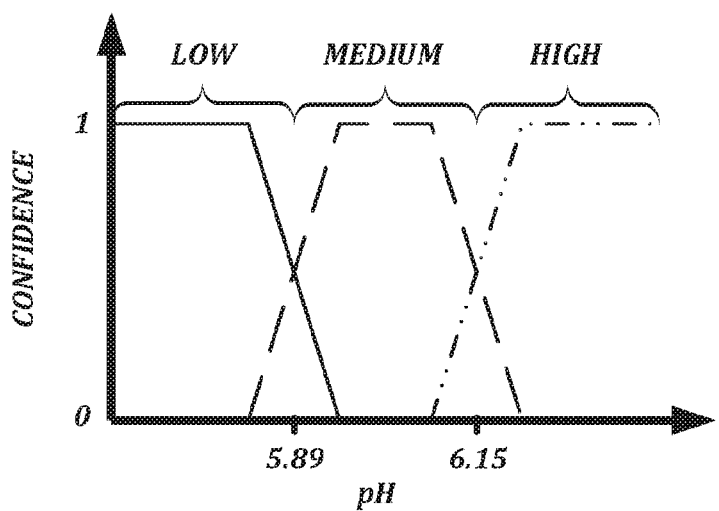
Figure 5C:
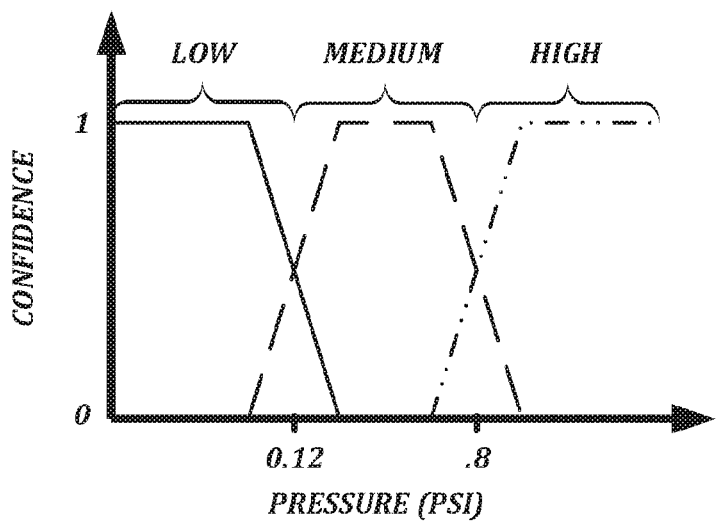

FIGS. 5A-5C are charts that illustrate examples of the assignment of fuzzy linguistic values according to various aspects of the present disclosure. In each of the charts, the horizontal axis represents a continuum of sensor values and is not to scale, and the vertical axis represents a level of confidence that a given linguistic value is associated with the sensor value on the horizontal axis. The level of confidence ranges from zero, indicating certainty that the associated condition is not present, to one, indicating certainty that the associated condition is present.

FIG. 5A illustrates an example of the assignment of fuzzy linguistic values to an oxygen saturation percentage ($SO_2$) sensor value. Three possible fuzzy linguistic values are illustrated: an $SO_2$ low linguistic value (illustrated by the solid line), an $SO_2$ medium linguistic value (illustrated by the regularly broken line), and an $SO_2$ high linguistic value (illustrated by the irregularly broken line). For the $SO_2$ low linguistic value, confidence starts at one, then falls off starting at a point before 60%, and ends up at zero after 60%. For the $SO_2$ medium linguistic value, confidence starts at zero, then starts rising at a point before 60%, and reaches one at a point between 60% and 85%. Confidence then starts falling at a subsequent point between 60% and 85%, and ends up at zero after 85%. For the $SO_2$ high linguistic value, confidence starts at zero, then begins to rise at a point before 85%, and ends up at one at a point after 85%. This results in $SO_2$ values below 60% to be associated with the $SO_2$ low linguistic value, $SO_2$ values between 60% and 85% to be associated with the $SO_2$ medium linguistic value, and $SO_2$ values above 85% to be associated with the $SO_2$ high linguistic value. The particular crossover values of 60% and 85% are an example only, and in some embodiments, these values may be lower or higher as appropriate. For example, the values of 60% and 85% may be useful for an embodiment in which $SaO_2$ (arterial oxygen saturation) is measured, while different values may be used for an embodiment in which $SvO_2$ (venous oxygen saturation) is measured.

FIG. 5B illustrates an example of the assignment of fuzzy linguistic values to a pH sensor value. Three possible fuzzy linguistic values are illustrated: a pH low linguistic value (illustrated by the solid line), a pH medium linguistic value (illustrated by the regularly broken line), and a pH high linguistic value (illustrated by the irregularly broken line). For the pH low linguistic value, confidence starts at one, then falls off starting at a point before 5.89, and ends up at zero after 5.89. For the pH medium linguistic value, confidence starts at zero, then starts rising at a point before 5.89, and reaches one at a point between 5.89 and 6.15. Confidence then starts falling at a subsequent point between 5.89 and 6.15, and ends up at zero after 6.15. For the pH high linguistic value, confidence starts at zero, then begins to rise at a point before 6.15, and ends up at one at a point after 6.15. This results in pH values below 5.89 to be associated with the pH low linguistic value, pH values between 5.89 and 6.15 to be associated with the pH medium linguistic value, and pH values above 6.15 to be associated with the pH high linguistic value.

FIG. 5C illustrates an example of the assignment of fuzzy linguistic values to a pressure sensor value. Three possible fuzzy linguistic values are illustrated: a pressure low linguistic value (illustrated by the solid line), a pressure medium linguistic value (illustrated by the regularly broken line), and a pressure high linguistic value (illustrated by the irregularly broken line). For the pressure low linguistic value, confidence starts at one, then falls off starting at a point before 0.12 psi, and ends up at zero after 0.12 psi. For the pressure medium linguistic value, confidence starts at zero, then starts rising at a point before 0.12 psi, and reaches one at a point between 0.12 psi and 0.8 psi. Confidence then starts falling at a subsequent point between 0.12 psi and 0.8 psi, and ends up at zero after 0.8 psi. For the pressure high linguistic value, confidence starts at zero, then begins to rise at a point before 0.8 psi, and ends up at one at a point after 0.8 psi. This results in pressure values below 0.12 psi to be associated with the pressure low linguistic value, pressure values between 0.12 psi and 0.8 psi to be associated with the pressure medium linguistic value, and pressure values above 0.8 psi to be associated with the pressure high linguistic value.

Though linear transitions between and within the high confidence regions and the low confidence regions are illustrated, in some embodiments, nonlinear transitions may be used, thereby moving the cross-over points which separate the linguistic values. Also, though the particular values listed above were determined experimentally to be appropriate for use in detecting arterial catheter status for neonates, they are examples only, and in some embodiments, other values may be used. At each transition point between linguistic values, a less than, less than or equal to, greater than, or greater than or equal to relationship may be used as appropriate. In some embodiments, particular values for these transition points may be modified by a user during use in order to adjust the sensitivity of the determinations to an appropriate level.

Figure 6A:
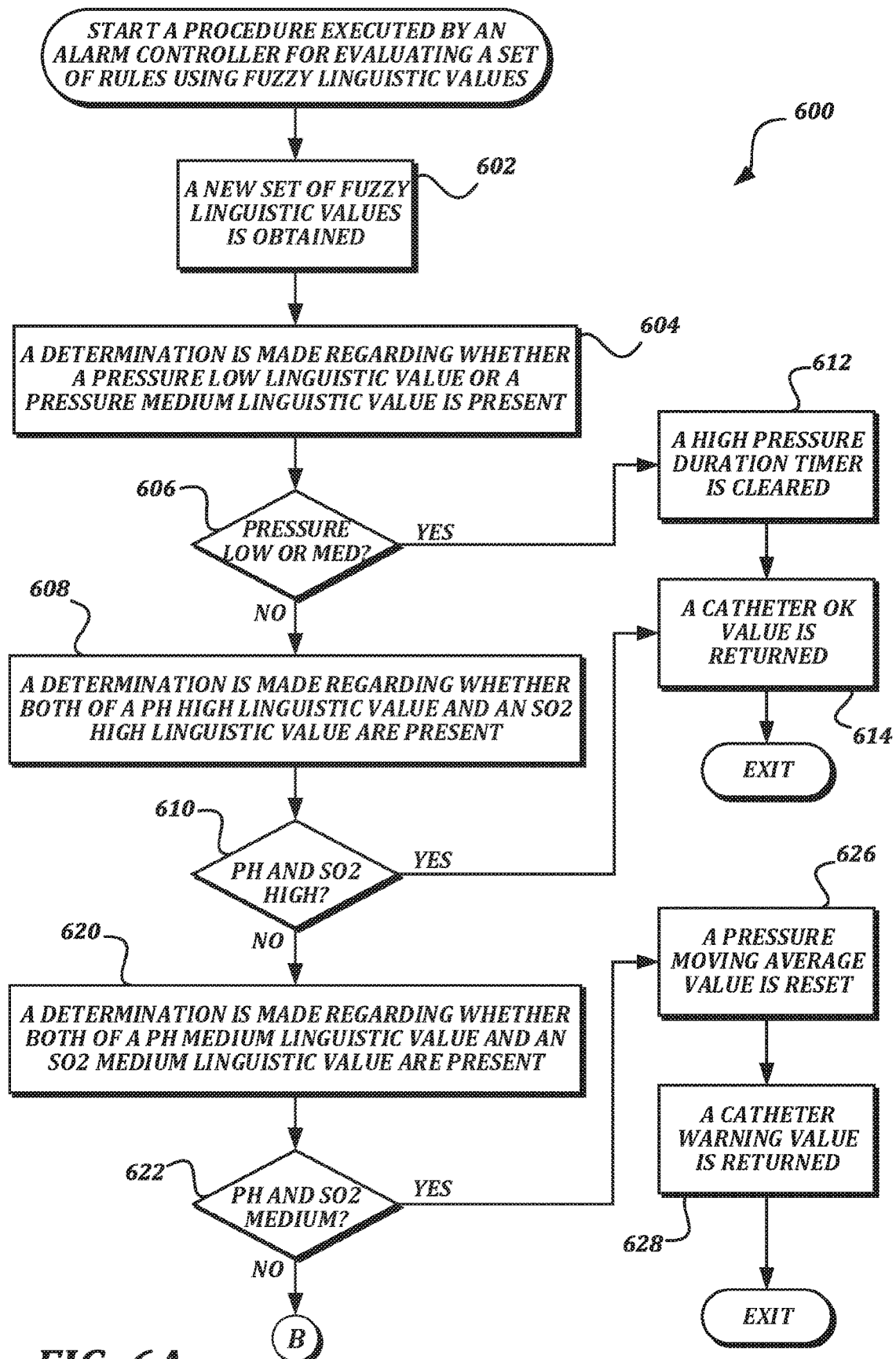
FIGS. 6A-6B are a flowchart that illustrates an example embodiment of a procedure executed by an alarm controller for evaluating a set of rules using fuzzy linguistic values according to various aspects of the present disclosure.
Figure 6B:
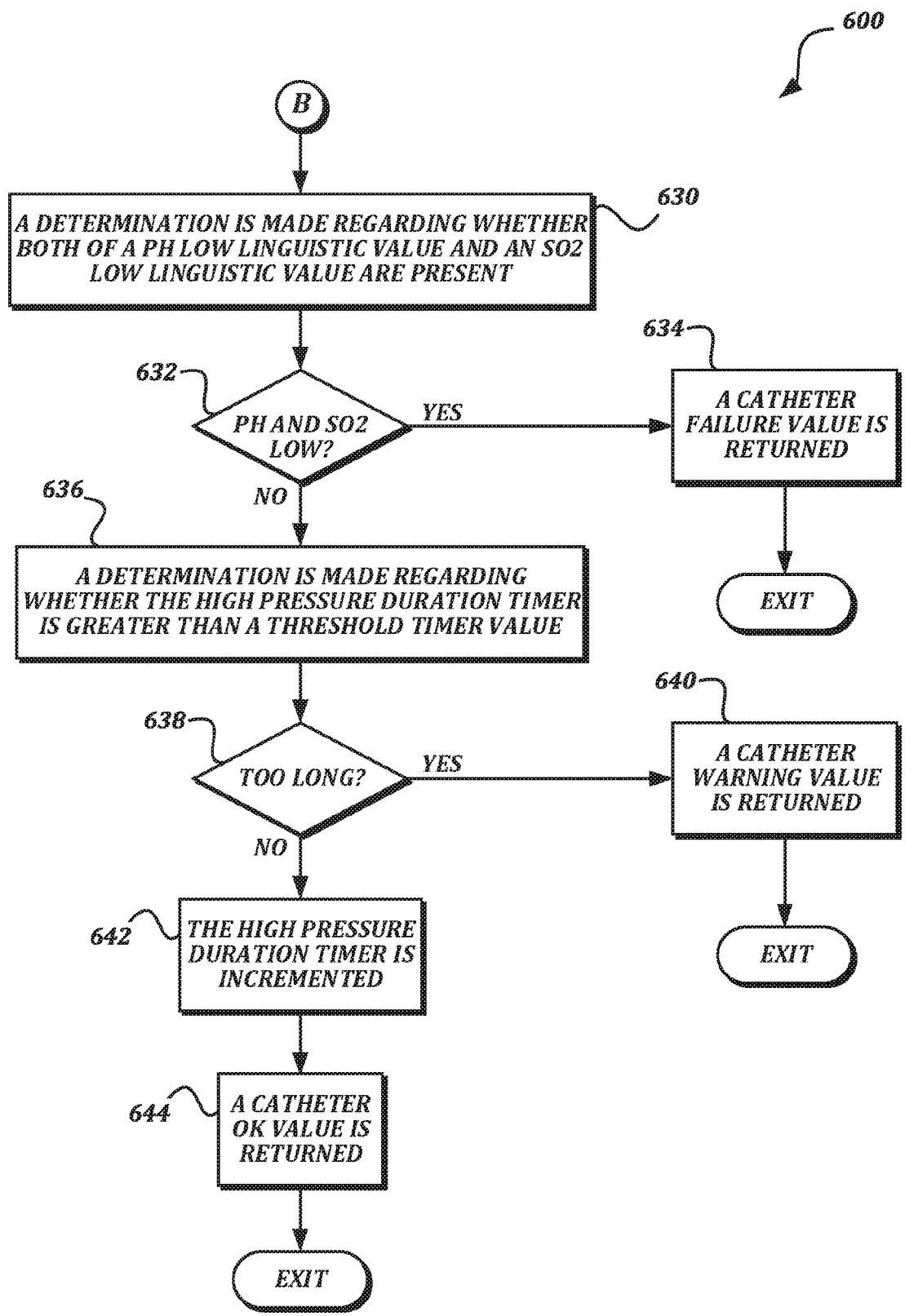

Returning to FIG. 4A, the method 400 then proceeds to a continuation terminal ("terminal B"). From terminal B (FIG. 4B), the method 400 proceeds to procedure block 414, where the alarm controller 210 evaluates a set of rules using the fuzzy linguistic values and, optionally, a set of previously stored fuzzy linguistic values. An output of the procedure is a catheter status value. In some embodiments, the catheter status value may be a catheter OK value, a catheter warning value, or a catheter failed value. In some embodiments, these values may be represented by fuzzy logic linguistic values. In some embodiments, these values may be represented by a numerical confidence value that is then compared to thresholds to determine whether a catheter OK value, a catheter warning value, or a catheter failed value is indicated. In some embodiments, the procedure called by procedure block 414 may store status information that persists between multiple loops of the method 400. Any suitable procedure may be used to evaluate a set of rules using the fuzzy linguistic values. One example procedure is illustrated in FIGS. 6A-6B and is described in further detail below.

After the procedure in procedure block 414 returns a catheter status value, the method 400 proceeds to decision block 416, where a test is performed to determine whether the catheter status value is a catheter OK value indicating that the catheter has been confirmed to be correctly placed. If the catheter status value is a catheter OK value, then the result of the test at decision block 416 is YES, and the method 400 proceeds to decision block 420. Otherwise, if the catheter status value is not a catheter OK value, then the result of the test at decision block 416 is NO, and the method 400 proceeds to block 418.

At block 418, the alarm controller 210 causes an alert to be presented. The alarm controller may cause the alert to be presented by transmitting a command to one or more alarm presentation devices 216 of the pump system 102, by transmitting a command to a remote computing device 218 via the network interface 214 of the pump system 102, or both. The alert itself could be a visual indicator to be presented by an indicator light or a display, a tone to be played by a loudspeaker, or both. In some embodiments, the type of alert presented may be determined by the catheter status value. For example, if the catheter status value is a catheter warning value, a first type of indicator may be displayed and/or a first tone may be played, while if the catheter status value is a catheter failed value, a second type of indicator may be displayed and/or a second tone may be played. The first type of indicator and the second type of indicator may differ by color (e.g., the first type of indicator may be yellow and the second type of indicator may be red), size, (e.g., the first type of indicator may be smaller than the second type of indicator), text description, brightness, or in any other suitable way. Likewise, the first tone and the second tone may differ by pitch, volume, rate of repetition, spoken message, or in any other suitable way. In some embodiments, the tone of an alert may change over time in order to draw attention to the alert if it is not cleared in a timely manner.

At block 420, a determination is made regarding whether the method 400 should continue. In some embodiments, the method 400 may end after any alert is presented by block 418, and may only loop or restart if manual intervention takes place to clear the alert. In some embodiments, the method 400 may end after a catheter failure alert is presented by block 418, but may automatically continue if a catheter warning alert is presented or the catheter is OK. In some embodiments, the alert may be automatically cleared or silenced after a predetermined amount of time if method 400 does continue. In some embodiments, the particular behavior at decision block 420 made may be configurable by a user. If it is determined that the method 400 should continue, then the result of decision block 420 is YES, and the method 400 returns to terminal A. Otherwise, if it is determined that the method 400 should end, then the result of decision block 420 is NO, and the method 400 proceeds to an end block and terminates.

FIGS. 6A-6B are a flowchart that illustrates an example embodiment of a procedure executed by an alarm controller for evaluating a set of rules using fuzzy linguistic values according to various aspects of the present disclosure. The procedure 600 is an example of a procedure suitable for use at block 414 of FIG. 4B. One should note that though passive voice is used in the flowchart and in the following description to help clarify the description, it should be assumed that, unless specifically stated otherwise, the actions described are being performed by the alarm controller 210 (or the alarm controller 210 interacting with other components of the pump system 102).

The illustrated embodiment of the procedure 600 accepts as input fuzzy linguistic values that represent a pressure linguistic value, a pH linguistic value, and an $SO_2$ linguistic value. The possible values for the pressure linguistic value are a pressure high linguistic value, a pressure medium linguistic value, and a pressure low linguistic value. The possible values for the pH linguistic value are a pH high linguistic value, a pH medium linguistic value, and a pH low linguistic value. The possible values for the $SO_2$ linguistic value are an $SO_2$ high linguistic value, an $SO_2$ medium linguistic value, and an $SO_2$ low linguistic value. In some embodiments, one fuzzy linguistic value will be provided as input for each type of data. For example, an input set of fuzzy linguistic values will include only one value selected from the pressure high linguistic value, the pressure medium linguistic value, and the pressure low linguistic value; only one value selected from the pH high linguistic value, the pH medium linguistic value, and the pH low linguistic value; and only one value selected from the $SO_2$ high linguistic value, the $SO_2$ medium linguistic value, and the $SO_2$ low linguistic value. In some embodiments, the procedure 600 may receive the sensor values themselves as input, and may either determine the fuzzy linguistic values based thereon, or may directly compare the sensor values to threshold values in making its determinations without formally assigning fuzzy linguistic values.

Beginning in FIG. 6A, from a start block, the procedure 600 advances to block 602, where a new set of fuzzy linguistic values is obtained. In some embodiments, the new set of fuzzy linguistic values may be the result of block 412 of the method 400 described above. In some embodiments, the new set of fuzzy linguistic values may be retrieved from the memory 212, in which case the new set of fuzzy linguistic values may be the latest set of fuzzy linguistic values in a stored time series.

Next, at block 604, a determination is made regarding whether a pressure low linguistic value or a pressure medium linguistic value is present. Determining whether a particular fuzzy linguistic value is present comprises determining whether the particular value is the value provided in the set of fuzzy linguistic values for that type of information. In other words, to determine whether a pressure low linguistic value is present, a determination is made regarding whether the pressure linguistic value in the set of fuzzy linguistic values is the pressure low linguistic value (instead of the pressure medium linguistic value or the pressure high linguistic value). If the pressure low linguistic value is present or the pressure medium linguistic value is present, then the result of subsequent decision block 606 is YES, and the procedure 600 advances to block 612, where a high pressure duration timer is cleared, and then to block 614. The high pressure duration time and block 614 are described separately below. If neither the pressure low linguistic value nor the pressure medium linguistic value is present (in other words, if the pressure high linguistic value is present), then the result of decision block 606 is NO, and the procedure 600 advances to block 608. One of ordinary skill in the art will recognize that determining that neither a pressure low linguistic value is present nor a pressure medium linguistic value is present is equivalent to determining that a pressure high linguistic value is present, and that determining that either a pressure low linguistic value is present or a pressure medium linguistic value is present is equivalent to determining that a pressure high linguistic value is not present.

At block 608, a determination is made regarding whether both of a pH high linguistic value and an $SO_2$ high linguistic value are present. If both are present, then the result of subsequent decision block 610 is YES, and the procedure 600 advances to block 614. At block 614, the procedure 600 has determined that the rules indicate that the status of the catheter remains acceptable because either (1) the pressure is low or medium, or (2) the pressure is high, but both of the pH and the $SO_2$ are high as well. Accordingly, at block 614, a catheter OK value is returned as the result of the procedure 600, and the procedure 600 advances to an exit block and terminates.

Returning to decision block 610, if either the pH high linguistic value or the $SO_2$ high linguistic value is not present, then the result of decision block 610 is NO, and the procedure 600 advances to block 620. At block 620, a determination is made regarding whether both of a pH medium linguistic value and an $SO_2$ medium linguistic value are present. If both are present, then the result of subsequent decision block 622 is YES, and the procedure 600 advances to block 626. Otherwise, the result of decision block 622 is NO, and the procedure advances to ta continuation terminal ("terminal B").

At block 626, the procedure 600 has determined that the rules indicate that the catheter might have failed, or at least cannot be confirmed as either definitely being OK or definitely having failed. Accordingly, at block 626, a pressure moving average value is reset. The procedure 600 then advances to block 628, where a catheter warning value is returned as the result of the procedure 600, and the procedure 600 advances to an exit block and terminates.

From terminal B (FIG. 6B), the procedure 600 advances to block 630, where a determination is made regarding whether both of a pH low linguistic value and an $SO_2$ low linguistic value are present. If both are present, then the result of subsequent decision block 632 is YES, and the procedure 600 advances to block 634. At block 634, the procedure 600 has determined that the rules indicate that the catheter has failed. Accordingly, at block 634, a catheter failure value is returned as the result of the procedure 600, and the procedure 600 advances to an exit block and terminates.

Returning to decision block 632, if at least one of the pH low linguistic value and the $SO_2$ low linguistic value are missing, then the result of decision block 632 is NO, and the procedure 600 advances to block 636. At block 636, a determination is made regarding whether the high pressure duration timer is greater than a threshold timer value. The high pressure duration timer persists between executions of the procedure 600, and may be used to delay presentation of a warning when high pressure is detected in absence of a clear indication from the pH and $SO_2$ values that an alert should be presented. This can help the alarm controller 210 ignore transient high pressure conditions that are artifacts or otherwise do not actually indicate failure. As discussed above, the high pressure duration timer may be reset in a subsequent execution of the procedure 600 upon detection of a pressure low linguistic value or a pressure medium linguistic value.

If the high pressure duration timer is greater than the threshold timer value, then the result of subsequent decision block 638 is YES, and the procedure 600 advances to block 640. At block 640, a catheter warning value is returned as the result of the procedure 600, and the procedure 600 advances to an exit block and terminates. In some embodiments, the catheter warning value at block 640 may be the same value as the catheter warning value at block 628. In some embodiments, the catheter warning values in these two blocks may be different to allow distinct alarms to be presented depending on how the warning was triggered.

Returning to decision block 638, if the high pressure duration timer is not greater than the threshold timer value, then the result of decision block 638 is NO, and the procedure 600 advances to block 642. At block 642, the high pressure duration timer is incremented. In some embodiments, incrementing the high pressure duration timer may include a count of a number of times the procedure 600 has executed, and the threshold timer value may be a predetermined number of times of execution. In some embodiments, the high pressure duration timer may include a timestamp generated when the timer is started, and may be represented by an elapsed time between the timestamp and a current time. In such an embodiment, a timer value may not actually be incremented at block 642, but instead the timestamp value may be set the first time the procedure 600 arrives at block 642. The determination at block 636 may then be based on a comparison of a timestamp of the first time arriving at block 642 and a current time.

The procedure 600 then advances to block 644, where a catheter OK value is returned as a result of the procedure 600, and then advances to an exit block where it terminates. Even though a catheter OK value is returned at block 644, subsequent executions of the procedure 600 by the method 400 will continue to check if the pressure has been high for too long, and if so, will advance to block 640 instead of blocks 642-644.

The method 400 and procedure 600 are primarily described above as operating contemporaneously with the collection of the sensor data. In some embodiments, the method 400 and procedure 600 could instead operate over previously stored sensor data, either to study archived data, to provide a time delay to the alerts, or to perform the analysis remotely from the collection of the data, if desirable.

Figure 7:
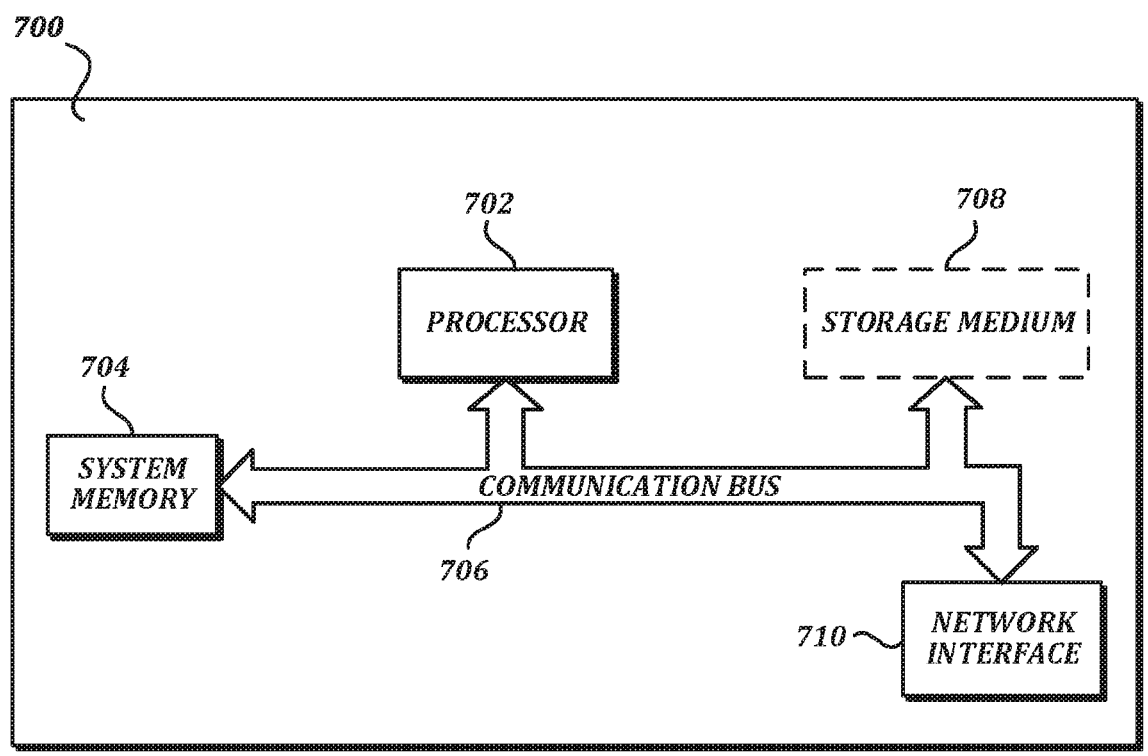
FIG. 7 is a block diagram that illustrates aspects of an exemplary computing device 700 appropriate for use as a computing device of the present disclosure.

FIG. 7 is a block diagram that illustrates aspects of an exemplary computing device 700 appropriate for use as a computing device of the present disclosure. While multiple different types of computing devices were discussed above, the exemplary computing device 700 describes various elements that are common to many different types of computing devices. While FIG. 7 is described with reference to a computing device that is implemented as a device on a network, the description below is applicable to servers, personal computers, mobile phones, smart phones, tablet computers, embedded computing devices, and other devices that may be used to implement portions of embodiments of the present disclosure. Moreover, those of ordinary skill in the art and others will recognize that the computing device 700 may be any one of any number of currently available or yet to be developed devices.

In its most basic configuration, the computing device 700 includes at least one processor 702 and a system memory 704 connected by a communication bus 706. Depending on the exact configuration and type of device, the system memory 704 may be volatile or nonvolatile memory, such as read only memory ("ROM"), random access memory ("RAM"), EEPROM, flash memory, or similar memory technology. Those of ordinary skill in the art and others will recognize that system memory 704 typically stores data and/or program modules that are immediately accessible to and/or currently being operated on by the processor 702. In this regard, the processor 702 may serve as a computational center of the computing device 700 by supporting the execution of instructions.

As further illustrated in FIG. 7, the computing device 700 may include a network interface 710 comprising one or more components for communicating with other devices over a network. Embodiments of the present disclosure may access basic services that utilize the network interface 710 to perform communications using common network protocols. The network interface 710 may also include a wireless network interface configured to communicate via one or more wireless communication protocols, such as WiFi, 2G, 3G, LTE, WiMAX, Bluetooth, Bluetooth low energy, and/or the like. As will be appreciated by one of ordinary skill in the art, the network interface 710 illustrated in FIG. 7 may represent one or more wireless interfaces or physical communication interfaces described and illustrated above with respect to particular components of the system 100.

In the exemplary embodiment depicted in FIG. 7, the computing device 700 also includes a storage medium 708. However, services may be accessed using a computing device that does not include means for persisting data to a local storage medium. Therefore, the storage medium 708 depicted in FIG. 7 is represented with a dashed line to indicate that the storage medium 708 is optional. In any event, the storage medium 708 may be volatile or nonvolatile, removable or nonremovable, implemented using any technology capable of storing information such as, but not limited to, a hard drive, solid state drive, CD ROM, DVD, or other disk storage, magnetic cassettes, magnetic tape, magnetic disk storage, and/or the like.

The particulars shown herein are by way of example and for purposes of illustrative discussion of example embodiments of the present disclosure only and are presented in the cause of providing what is believed to be the most useful and readily understood description of the principles and conceptual aspects of various embodiments of the disclosure. In this regard, no attempt is made to show structural details in more detail than is necessary for the fundamental understanding of the disclosure, the description taken with the drawings and/or examples making apparent to those skilled in the art how the several forms of the disclosure may be embodied in practice.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

All of the references cited herein are incorporated by reference. Aspects of the disclosure can be modified, if necessary, to employ the systems, functions, and concepts of the above references and application to provide yet further embodiments of the disclosure. These and other changes can be made to the disclosure in light of the detailed description.

Specific elements of any foregoing embodiments can be combined or substituted for elements in other embodiments. Moreover, the inclusion of specific elements in at least some of these embodiments may be optional, wherein further embodiments may include one or more embodiments that specifically exclude one or more of these specific elements. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The embodiments of the invention in which an exclusive property or privilege is claimed are defined as follows:

1. A method of automatically monitoring a status of an intravenous catheter, the method comprising:
    receiving, by a processor of an alarm controller, a set of signals from at least one of a pH sensor and an oximeter located at a distal end of the intravenous catheter;
    performing, by the processor, a fuzzy logic analysis based on the signals to determine a catheter status value, wherein the fuzzy logic analysis comprises:
        assigning fuzzy linguistic values to values indicated by the set of signals; and
        determining the catheter status value based on the fuzzy linguistic values; and
    in response to determining that the catheter status value indicates failure of the intravenous catheter, causing, by the processor, an alert to be presented;
    wherein the set of signals includes a signal from a pressure sensor;
    wherein the values indicated by the set of signals include a pH value, and wherein the fuzzy linguistic values include at least one of a pH high linguistic value, a pH medium linguistic value, and a pH low linguistic value;
    wherein the values indicated by the set of signals include an oxygen saturation percentage (SO2) value, and wherein the fuzzy linguistic values include at least one of an SO2 high linguistic value, an SO2 medium linguistic value, and an SO2 low linguistic value;
    wherein the values indicated by the set of signals include a pressure value, and wherein the fuzzy linguistic values include at least one of a pressure high linguistic value, a pressure medium linguistic value, and a pressure low linguistic value;
    wherein assigning fuzzy linguistic values to values indicated by the set of signals includes at least one of assigning a fuzzy linguistic value to the pH value, assigning a fuzzy linguistic value to the SO2 value, or assigning a fuzzy linguistic value to the pressure value;
    wherein assigning the fuzzy linguistic value to the pH value includes:
        assigning the pH high linguistic value in response to determining that the pH value is greater than or equal to 6.15;
        assigning the pH medium linguistic value in response to determining that the pH value is between 5.89 and 6.15; and
        assigning the pH low linguistic value in response to determining that the pH value is less than or equal to 5.89;
    wherein assigning the fuzzy linguistic value to the SO2 value includes:
        assigning the SO2 high linguistic value in response to determining that the SO2 value is greater than or equal to 85%;
        assigning the SO2 medium linguistic value in response to determining that the SO2 value is between 60% and 85%; and
        assigning the SO2 low linguistic value in response to determining that the SO2 value is less than or equal to 60%; and
    wherein assigning the fuzzy linguistic value to the pressure value includes:
        assigning the pressure high linguistic value in response to determining that the pressure value is greater than or equal to 0.8 psi;
        assigning the pressure medium linguistic value in response to determining that the pressure value is between 0.12 psi and 0.8 psi; and
        assigning the pressure low linguistic value in response to determining that the pressure value is less than or equal to 0.12 psi.

2. The method of claim 1, wherein the fuzzy logic analysis further comprises:
    determining a rate of change of at least one of the values indicated by the set of signals; and
    assigning a fuzzy linguistic value to the rate of change.

3. The method of claim 1, wherein determining the catheter status value based on the fuzzy linguistic values includes:
    determining that the catheter status value is a catheter OK value when the fuzzy linguistic values include a pressure low linguistic value, a pressure medium linguistic value, or a combination of a pH high linguistic value and an SO2 high linguistic value.

4. The method of claim 1, wherein determining the catheter status value based on the fuzzy linguistic values includes:
  determining that the catheter status value is a catheter warning value when the fuzzy linguistic values include all of a pressure high linguistic value, a pH medium linguistic value, and an SO2 medium linguistic value.

5. The method of claim 1, wherein determining the catheter status value based on the fuzzy linguistic values includes:
  determining that the catheter status value is a catheter failure value when the fuzzy linguistic values include all of a pressure high linguistic value, a pH low linguistic value, and an SA02 low linguistic value.

6. The method of claim 1, wherein determining the catheter status value based on the fuzzy linguistic values includes:
  in response to determining that the fuzzy linguistic values include a pressure high linguistic value:
    determining an amount of time for which the pressure high linguistic value has been present; and
    determining that the catheter status value is a catheter warning value when the pressure high linguistic value has been present for longer than a threshold amount of time.

7. The method of claim 1, further comprising:
  storing a set of values for the set of signals as an old set of values;
  assigning fuzzy linguistic values to the old set of values;
  receiving a new set of values for the set of signals;
  assigning fuzzy linguistic values to the new set of values; and
  determining the catheter status value based on the fuzzy linguistic values of the old set of values and the fuzzy linguistic values of the new set of values.

8. A method of automatically monitoring a status of an intravenous catheter, the method comprising:
  receiving, by a processor of an alarm controller, a set of signals from at least one of a pH sensor and an oximeter located at a distal end of the intravenous catheter;
  performing, by the processor, a fuzzy logic analysis based on the signals to determine a catheter status value, wherein the fuzzy logic analysis comprises:
    assigning fuzzy linguistic values to values indicated by the set of signals; and
    determining the catheter status value based on the fuzzy linguistic values; and
  in response to determining that the catheter status value indicates failure of the intravenous catheter, causing, by the processor, an alert to be presented;
  wherein the set of signals includes a signal from a pressure sensor;
  wherein the values indicated by the set of signals include a pH value, and wherein the fuzzy linguistic values include at least one of a pH high linguistic value, a pH medium linguistic value, and a pH low linguistic value;
  wherein the values indicated by the set of signals include an oxygen saturation percentage (SO2) value, and wherein the fuzzy linguistic values include at least one of an SO2 high linguistic value, an SO2 medium linguistic value, and an SO2 low linguistic value;
  wherein the values indicated by the set of signals include a pressure value, and wherein the fuzzy linguistic values include at least one of a pressure high linguistic value, a pressure medium linguistic value, and a pressure low linguistic value; and
  wherein determining the catheter status value based on the fuzzy linguistic values includes at least one of:
    determining that the catheter status value is a catheter OK value when the fuzzy linguistic values include a pressure low linguistic value, a pressure medium linguistic value, or a combination of a pH high linguistic value and an SO2 high linguistic value;
    determining that the catheter status value is a catheter warning value when the fuzzy linguistic values include all of a pressure high linguistic value, a pH medium linguistic value, and an SO2 medium linguistic value; or
    determining that the catheter status value is a catheter failure value when the fuzzy linguistic values include all of a pressure high linguistic value, a pH low linguistic value, and an SA02 low linguistic value.

9. The method of claim 8, wherein assigning fuzzy linguistic values to values indicated by the set of signals includes:
  assigning a pH high linguistic value to a pH value greater than or equal to 6.15;
  assigning a pH medium linguistic value to a pH value between 5.89 and 6.15; and
  assigning a pH low linguistic value to a pH value less than or equal to 5.89.

10. The method of claim 8, wherein assigning fuzzy linguistic values to values indicated by the set of signals includes:
  assigning an SO2 high linguistic value to an SO2 value greater than or equal to 85%;
  assigning an SO2 medium linguistic value to an SO2 value between 60% and 85%; and
  assigning an SO2 low linguistic value to an SO2 value less than or equal to 60%.

11. The method of claim 8, wherein assigning fuzzy linguistic values to values indicated by the set of signals includes:
  assigning a pressure high linguistic value to a pressure value greater than or equal to 0.8 psi;
  assigning a pressure medium linguistic value to a pressure value between 0.12 psi and 0.8 psi; and
  assigning a pressure low linguistic value to a pressure value less than or equal to 0.12 psi.

12. The method of claim 8, wherein the fuzzy logic analysis further comprises:
  determining a rate of change of at least one of the values indicated by the set of signals; and
  assigning a fuzzy linguistic value to the rate of change.

13. The method of claim 8, wherein determining the catheter status value based on the fuzzy linguistic values includes:
  in response to determining that the fuzzy linguistic values include a pressure high linguistic value:
    determining an amount of time for which the pressure high linguistic value has been present; and
    determining that the catheter status value is a catheter warning value when the pressure high linguistic value has been present for longer than a threshold amount of time.

14. The method of claim 8, further comprising:
  storing a set of values for the set of signals as an old set of values;
  assigning fuzzy linguistic values to the old set of values;
  receiving a new set of values for the set of signals;
  assigning fuzzy linguistic values to the new set of values; and determining the catheter status value based on the fuzzy linguistic values of the old set of values and the fuzzy linguistic values of the new set of values.

15. A method of automatically monitoring a status of an intravenous catheter, the method comprising:
receiving, by a processor of an alarm controller, a set of signals from at least one of a pH sensor and an oximeter located at a distal end of the intravenous catheter;
performing, by the processor, a fuzzy logic analysis based on the signals to determine a catheter status value, wherein the fuzzy logic analysis comprises:
assigning fuzzy linguistic values to values indicated by the set of signals; and
determining the catheter status value based on the fuzzy linguistic values; and
in response to determining that the catheter status value indicates failure of the intravenous catheter, causing, by the processor, an alert to be presented;
wherein the set of signals includes a signal from a pressure sensor;
wherein the values indicated by the set of signals include a pH value, and wherein the fuzzy linguistic values include at least one of a pH high linguistic value, a pH medium linguistic value, and a pH low linguistic value;
wherein the values indicated by the set of signals include an oxygen saturation percentage (SO2) value, and wherein the fuzzy linguistic values include at least one of an SO2 high linguistic value, an SO2 medium linguistic value, and an SO2 low linguistic value;
wherein the values indicated by the set of signals include a pressure value, and wherein the fuzzy linguistic values include at least one of a pressure high linguistic value, a pressure medium linguistic value, and a pressure low linguistic value; and
wherein determining the catheter status value based on the fuzzy linguistic values includes:
in response to determining that the fuzzy linguistic values include a pressure high linguistic value:
determining an amount of time for which the pressure high linguistic value has been present; and
determining that the catheter status value is a catheter warning value when the pressure high linguistic value has been present for longer than a threshold amount of time.

16. The method of claim 15, wherein assigning fuzzy linguistic values to values indicated by the set of signals includes:
assigning a pH high linguistic value to a pH value greater than or equal to 6.15;
assigning a pH medium linguistic value to a pH value between 5.89 and 6.15; and
assigning a pH low linguistic value to a pH value less than or equal to 5.89.

17. The method of claim 15, wherein assigning fuzzy linguistic values to values indicated by the set of signals includes:
assigning an SO2 high linguistic value to an SO2 value greater than or equal to 85%;
assigning an SO2 medium linguistic value to an SO2 value between 60% and 85%; and
assigning an SO2 low linguistic value to an SO2 value less than or equal to 60%.

18. The method of claim 15, wherein assigning fuzzy linguistic values to values indicated by the set of signals includes:
assigning a pressure high linguistic value to a pressure value greater than or equal to 0.8 psi;
assigning a pressure medium linguistic value to a pressure value between 0.12 psi and 0.8 psi; and
assigning a pressure low linguistic value to a pressure value less than or equal to 0.12 psi.

19. The method of claim 15, wherein the fuzzy logic analysis further comprises:
determining a rate of change of at least one of the values indicated by the set of signals; and
assigning a fuzzy linguistic value to the rate of change.

20. The method of claim 15, wherein determining the catheter status value based on the fuzzy linguistic values includes:
determining that the catheter status value is a catheter OK value when the fuzzy linguistic values include a pressure low linguistic value, a pressure medium linguistic value, or a combination of a pH high linguistic value and an SO2 high linguistic value.

21. The method of claim 15, wherein determining the catheter status value based on the fuzzy linguistic values includes:
determining that the catheter status value is a catheter warning value when the fuzzy linguistic values include all of a pressure high linguistic value, a pH medium linguistic value, and an SO2 medium linguistic value.

22. The method of claim 15, wherein determining the catheter status value based on the fuzzy linguistic values includes:
determining that the catheter status value is a catheter failure value when the fuzzy linguistic values include all of a pressure high linguistic value, a pH low linguistic value, and an SA02 low linguistic value.

23. The method of claim 15, further comprising:
storing a set of values for the set of signals as an old set of values;
assigning fuzzy linguistic values to the old set of values;
receiving a new set of values for the set of signals;
assigning fuzzy linguistic values to the new set of values; and
determining the catheter status value based on the fuzzy linguistic values of the old set of values and the fuzzy linguistic values of the new set of values.

* * * * *